(12) United States Patent

Vipperman et al.

(10) Patent No.: US 12,672,797 B2

(45) Date of Patent: Jul. 7, 2026

(54) HEARING SCREENING AND AMPLIFICATION DEVICE

(71) Applicant: UNIVERSITY OF PITTSBURGH—OF THE COMMONWEALTH SYSTEM OF HIGHER EDUCATION, Pittsburgh, PA (US)

(72) Inventors: Jeffrey Vipperman, Pittsburgh, PA (US); Catherine Palmer, Pittsburgh, PA (US); Erik Rauterkus, Pittsburgh, PA (US); Jacalynn Ona Sharp, Silver Spring, MD (US); Christopher Dumm, Verona, PA (US); Joseph Lyle Koch, Ventura, CA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 525 days.

(21) Appl. No.: 18/550,154

(22) PCT Filed: Mar. 18, 2022

(86) PCT No.: PCT/US2022/020873

§ 371 (c)(1),
(2) Date: Sep. 12, 2023

(87) PCT Pub. No.: WO2022/197997

PCT Pub. Date: Sep. 22, 2022

(65) Prior Publication Data

US 2024/0156370 A1    May 16, 2024

Related U.S. Application Data

(60) Provisional application No. 63/162,932, filed on Mar. 18, 2021.

(51) Int. Cl.
| | |
|---|---|
| *H04R 25/00* | (2006.01) |
| *A61B 5/12* | (2006.01) |
(Continued)

(52) U.S. Cl.
CPC .............. *A61B 5/123* (2013.01); *A61B 5/742* (2013.01); *A61B 5/7475* (2013.01); *H04R 29/00* (2013.01); *H04R 2430/01* (2013.01)

(58) Field of Classification Search
CPC ....... A61B 5/123; A61B 5/742; A61B 5/7475; H04R 2430/01; H04R 29/00
(Continued)

(56) References Cited

U.S. PATENT DOCUMENTS

| | | |
|---|---|---|
| 2004/0039299 A1 | 2/2004 | Harrison et al. |
| 2008/0187145 A1 | 8/2008 | Burrows et al. |
(Continued)

*Primary Examiner* — Phylesha Dabney

(74) *Attorney, Agent, or Firm* — Philip E. Levy; Eckert Seamans Cherin & Mellott, LLC

(57) ABSTRACT

A portable hearing screening and amplification device structured to be coupled to a headset includes: a housing, a plurality of buttons, a plurality of indicators, a microphone circuit, an output circuit, a power source, and a controller. Upon passing a background noise test, the portable hearing screening and amplification device is structured to transmit a plurality of hearing screening tones to the headset for a user for testing of the plurality of hearing screening tones and complete the hearing screening based on responses of the user related to the plurality of hearing screening tones, the responses including a number of hearing screening tones that the user has perceived during the hearing screening. Based on a determination that the number of hearing screening tones perceived is less than a prerequisite number, the portable hearing screening and amplification device is further structured to switch to amplification mode and provide amplification.

20 Claims, 12 Drawing Sheets

(51) Int. Cl.
    *A61B 5/00*          (2006.01)
    *H04R 29/00*       (2006.01)

(58) Field of Classification Search
    USPC ........................................................ 381/60
    See application file for complete search history.

(56)                     References Cited

U.S. PATENT DOCUMENTS

| 2010/0119093 | A1 | 5/2010 | Uzuanis et al. |
| 2016/0081595 | A1 | 3/2016 | Hui et al. |
| 2020/0315544 | A1 | 10/2020 | Levine |

HEARING SCREENING AND AMPLIFICATION DEVICE

CROSS-REFERENCE TO RELATED APPLICATION

This patent application claims the priority benefit under 35 U.S.C. § 119(e) of U.S. Provisional Application No. 63/162,932, filed on Mar. 18, 2021, the contents of which are herein incorporated by reference.

GOVERNMENT CONTRACT

This application is a U.S. National Phase of International Application No. PCT/US2022/020873, filed on Mar. 18, 2022, which claims the priority benefit under 35 U.S.C. § 119 (e) of U.S. Provisional Application No. 63/162,932, filed on Mar. 18, 2021, the contents of which are herein incorporated by reference.

BACKGROUND OF THE INVENTION

1. Field of the Invention

The present invention relates to a hearing screening apparatus and, in particular, to a low-cost, easy-to-use hearing screening and amplification device that screens for hearing loss and/or provides hearing amplification.

2. Description of the Related Art

Undiagnosed, untreated hearing loss has been linked to increased social isolation, poor health outcomes and increased medical expenses. The World Health Organization (WHO) defines disabling hearing loss as having more than 35 $dB_{HL}$ (where HL stands for Hearing Level) average hearing loss and estimates that the number of people with disabling hearing loss has increased from 42 million in 1985 to 360 million in 2011. An estimated 38 million people in the United States live with hearing loss with only 20% of adults seeking the known treatment which includes the use of amplification.

The current standard of care for routine or emergency healthcare visits does not include hearing screening. One in eight people over the age of 12 in the U.S. has disabling hearing loss, and 50% of the population older than 75 suffer from disabling hearing loss. In the past 15 years, the number of Americans with hearing loss has doubled and is expected to continue to grow worldwide. Less than one in three patients with disabling hearing loss has been diagnosed, and thus are unable to notify their health care provider of their hearing loss condition. Conversations at a medical visit typically contain important questions regarding the patient's health and symptoms, e.g., medications prescribed, instructions regarding dosage and use for the medications, etc. The patient with unreported hearing loss may not hear or may misinterpret questions and directions. An individual with unreported, untreated hearing loss cannot fully participate in health care decisions and management. These are examples of use settings, but this device can be used in any situation where hearing needs to be screened and communication needs to be improved. Untreated hearing loss may be associated with over $20,000 per patient in increased healthcare costs over a 10-year period. Patients with untreated hearing loss experienced more inpatient stays and were at greater risk for 30-day hospital readmission. Patient readmissions stemming from hearing loss-related complications cost the U.S. healthcare industry an estimated $133 billion per year. Untreated hearing loss is estimated to cost the global healthcare industry nearly $750 billion per year.

Performing formal hearing testing for patients during patient visits is not practical for routine healthcare visits. Hearing testing typically requires a visit with an audiology specialist, requiring training that an average nurse or physician does not have. An audiologist first evaluates the ear canal and the ear drum (e.g., ear wax blockages, otitis, etc.) by otoscopy using a magnifying glass, light, and small cone. Then, the audiologist checks middle ear function and response using tympanometry, measuring the mobility of the ear drum. Audiometric hearing testing requires specialized facilities, equipment, and training, and is generally conducted in an audiometric sound-proof booth. A standard test is conducted in a sound-isolated booth using an audiometer, which plays single-frequency tones (i.e., pure tones) at various intensity levels to determine the quietest sound a patient can recognize. The quietest perceived sound is considered the threshold of hearing and this is established via air conduction signals which test the entire hearing system and bone conduction signals which bypass the outer and middle ear to test the inner ear (cochlea). An audiometer and headphones are required to produce the tones at various levels, and to play the tones at different frequencies (e.g., 250, 500, 1000, 1500, 2000, 3000, 4000, 6000, and 8000 Hz, etc.) and levels into each ear of the patient. The test results are then collected in an audiogram (i.e., a graph showing the threshold of hearing at each frequency for both ears) which may be used to prescribe hearing aids individualized to the patient's hearing loss (e.g., a type of hearing amplification for the patient). For example, if the patient has 40 dB of hearing loss at 2 kHz, a tone has to be at least 40 dB louder than the normal hearing threshold for the patient to perceive the tone in that ear.

However, sound booths are bulky, expensive (e.g., tens of thousands of dollars), and standard evaluations require a trained audiologist to conduct the hearing test. Audiology equipment is expensive and approximately 30 minutes are needed to conduct a proper hearing test. Such time commitment is not suitable for a routine healthcare visit during which a patient spends less than approximately 17 minutes with the physician. Further, a typical hearing test evaluates different aspects of the patient's hearing profile (e.g., air and bone conduction) using various equipment (e.g., audiometer, headset, bone vibrator, etc.). Further, the audiometers need to be routinely (e.g., at least annually as per the Occupational Safety and Health Administration) calibrated to ensure that the audiograms produced are accurate and reflective of the patients' actual hearing condition. The usage of audiometers in a full hearing health screening is costly to the patient and may not be feasible for every patient and produces more information than is needed to determine the need for hearing assistance during the health care appointment and the need for referral for comprehensive hearing testing.

An alternative to formal hearing testing is a hearing screening conducted with a purpose-built, portable hearing screener that is faster and more portable than an audiometer. The primary difference between the hearing screener and an audiometer is that the hearing screener identifies hearing loss on a pass-fail basis. However, while portable, and simpler than formal audiometric hearing testing, hearing screening is rarely provided during a healthcare visit. While hearing screening may be faster and easier than conducting audiometric testing, the screening results may be confounded by noise in the environment leaving the physician unsure of the need for hearing assistance and referral for further hearing health care. Further, hearing screeners may not be intuitive to use, resulting in the person administering the screening having to waste time to figure out how to use the device. Moreover, hearing screeners are also expensive (e.g., ranging from over $100 to $1,200), and require specially designed headphones to block out background noise and some specialized training to conduct the hearing screening. If a patient is identified as having hearing loss during the screening, a short-term treatment device (e.g., personal sound amplification products (PSAPs)) should be used. The use of PSAPs is rare during the healthcare visit even if the patient has been determined to have failed the hearing screening. Many offices are unsure what PSAP is safe to use since these devices are not regulated by the FDA. Thus, there are no devices available to healthcare professionals that simultaneously provide an easy-to-use method of hearing screening combined with a PSAP in order to address communication difficulties due to hearing loss during healthcare visits.

PSAPs cost between $40 to $350 and are not regulated as medical devices by the Food and Drug Administration. PSAPs are bulky and not designed for everyday use. PSAPs are not customized to an individual's hearing (e.g., it amplifies all frequencies the same amount for any level of sound). As such, they are not meant to replace individualized hearing solutions. Smart phones now include hearing screening and hearing assistance apps. However, sharing a personal smart phone during a healthcare visit with clinician may raise privacy and infection control concerns. Moreover, such a hearing screening app may not include an effective background noise checking system to perform hearing screening necessitating the need for the user to be in a quiet area. Furthermore, the limits of perception of audiometric screening tones in the midst of noise specific to health care facilities were not established until now and are headphone dependent. Characterization the frequency response and acoustic insertion loss of the headphones are essential steps in establishing the thresholds of these noise limits.

There is a strong need for a low-cost, low-profile, simple hearing device that any healthcare professional may use to perform hearing screening within, e.g., 90 seconds or less, and provide immediate short-term personal amplification at least for the duration of the healthcare visit.

SUMMARY OF THE INVENTION

Accordingly, it is an object of the present disclosure to provide a novel, low-cost, portable hearing device that combines hearing screening and personal hearing amplification functionalities. The hearing device in accordance with the present disclosure conducts accurate hearing screening, e.g., in a regular clinical setting with background noise by first performing a "Go/No Go" check of the background noise levels to ensure that they are within acceptable limits for screening. If it is determined that the user (a person being screened, e.g., a patient) fails the screening, the hearing device is easily convertible to provide non-custom amplification, where the volume can be controlled manually or automatically. As such, the hearing device may be used for hearing screening during a visit, and if the patient fails the hearing screening, the user may use the hearing device as an amplifier. Additionally, the hearing device in accordance with the present disclosure may reduce burden on the healthcare system by reducing hospital readmissions and medical adverse events by improving accuracy of communication related to discharge instructions by identifying hearing loss and providing an enhanced signal during these interactions. Screening and the experience of enhanced hearing may provide the opportunity for referral to appropriate hearing health care for customized hearing solutions that will benefit the individual in their everyday communication interactions.

These objects are achieved according to the embodiment of the present disclosure by providing a portable hearing screening and amplification device structured to be coupled to a headset, including: a housing, a plurality of buttons, a plurality of indicators, a microphone circuit, an output circuit, a power source, and a controller, where the plurality of buttons comprises a background noise test switch structured to enable a background noise test, a hearing screening switch structured to commence hearing screening based at least in part on passing of the background noise test, a volume adjuster structured to enable amplification based on volume control levels and adjust the volume of a speaker of the headset, a power button structured to turn on and off the hearing device, and a display button structured to activate the display circuit; and where the controller is coupled to the display circuit, the output circuit coupled to the speaker, the plurality of indicators, and the microphone circuit, and structured to control signal processing related to the microphone circuit, the display circuit, the output circuit, the hearing screening, and the amplification, where based on passing a background noise test, the portable hearing screening and amplification device is structured to transmit a plurality of hearing screening tones to the headset for a user for testing of the plurality of hearing screening tones, and complete the hearing screening based on responses of the user related to the plurality of hearing screening tones, the responses including a number of hearing screening tones that the user has perceived during the hearing screening; and where based on a determination that the number of hearing screening tones perceived by the user is less than a prerequisite number, the portable hearing screening and amplification device is further structured to switch to amplification mode and perform the amplification based on a volume control level of the volume adjuster.

In some examples, the portable hearing screening and amplification device is further structured to be used during a healthcare visit comprising inpatient stay, senior living intake assessment, emergency room visit, home health visit, or a routine check-up.

In some examples, the portable hearing screening and amplification device comprises a size less than or equal to a size of a hand-held device.

In some examples, the hearing screening including the testing of the plurality of screening tones is performed based on the preset timing sequence.

In some examples, the plurality of indicators includes a status indicator structured to indicate status of the portable hearing screening and amplification device, a plurality of hearing screening indicators structured to indicate respective testing result status of the plurality of hearing screening tones, and a power indicator structured to indicate power status of the portable hearing screening and amplification device.

In some examples, the plurality of hearing screening tones includes frequencies within a primary hearing range including 1 kHz, 2 kHz, and 4 kHz that are prone to hearing loss. In some examples, the plurality of hearing screening tones includes at least six screening tones comprising 1 kHz, 2 kHz, and 4 kHz such that only frequencies necessary for hearing screening are tested during a brief period less than or equal to 90 seconds. In some examples, a period of the testing of each hearing screening tone is less than or equal to 90 seconds.

In some examples, the controller includes a calibrated sound pressure level threshold derived from sound data collected from a plurality of environments and predetermined voltage levels associated with background noise thresholds and the plurality of environments. A background noise having sound pressure level above the calibrated sound pressure level threshold fails the background noise test and a background noise having the sound pressure level less than or equal to the calibrated sound pressure level thresholds passes the background noise test.

In some examples, at least one of the microphone circuit, the output circuit or the headset is calibrated to collect an output voltage of the microphone circuit for background noise test thresholds, the output circuit being calibrated to control output signal delivered to the headset, and the headset being calibrated to receive at least the plurality of hearing screening tones. The background noise test determines that the background noise detected falls within the background noise test thresholds, and the hearing screening is performed based upon the determination. The background noise test thresholds may be A-weighted to reflect human hearing spectrum.

In some examples, the controller includes a software configured to facilitate the background noise test, hearing screening and amplification and to control the plurality of indicators.

In some examples, the plurality of hearing screening tones includes six tones, three tones for each ear of the patient, and the prerequisite number is at least five to pass the hearing screening.

In another embodiment, a method for providing amplification and hearing screening using a portable hearing screening and amplification device coupled to a headset is provided. The method includes: turning on the portable hearing screening and amplification device comprising a housing, a plurality of buttons, a plurality of indicators, a display circuit, a microphone circuit, an output circuit, a power source, and a controller, where the plurality of buttons comprises a background noise test switch structured to activate a background noise test, a hearing screening switch structured to commence hearing screening based at least in part on passing of the background noise test, a volume adjuster for enabling amplification and adjusting a volume of a speaker of the headset, and a power button for turning on and off the portable hearing screening and amplification device, and the controller is coupled to the display circuit, the output circuit, the plurality of hearing screening indicators, the microphone circuit, the plurality of indicators and the speaker, and is structured to control signal processing related to the microphone circuit, the hearing screening, and the amplification. The method also includes activating a background noise test switch to determine that a screening location passes or fails the background noise test; transmitting, upon passing the background noise test, a plurality of hearing screening tones to a user via the headset for testing of each hearing screening tone; completing the hearing screening based on responses of the user related to the plurality of hearing screening tones, the responses including a number of hearing screening tones that the user has perceived during the hearing screening; determining that the user has perceived a requisite number of hearing screening tones; and based on a determination that the number of hearing screening tones perceived by the user is less than a prerequisite number, switching to amplification mode from hearing screening mode and performing the amplification based on a volume control level of the volume adjuster.

In some examples, the portable hearing screening and amplification device is further structured to be used during a healthcare visit comprising inpatient stay, senior living intake assessment, emergency room visit, home health visit, or a routine check-up. The portable hearing screening and amplification device includes a size less than or equal to a size of a hand-held device.

In some examples, the method also may include indicating at least one of status of the portable hearing screening and amplification device including pass or fail state of the background noise test, testing result status of the plurality of hearing screening tones or a power status of the portable hearing screening and amplification device.

In some examples, the controller includes a calibrated sound pressure level threshold derived from background noise sound data collected from a plurality of environments and predetermined voltage levels associated with background noise thresholds and the plurality of environments and wherein a background noise having sound pressure level above the calibrated sound pressure level threshold fails the background noise test and a background noise having the sound pressure level less than or equal to the calibrated sound pressure level thresholds passes the background noise test.

In another embodiment, a method for providing amplification and hearing screening using a portable hearing screening and amplification device coupled to a headset is provided. The method includes turning on the portable hearing screening and amplification device; activating a background noise test switch based on a user input to determine that a testing area passes or fails a background noise test; transmitting, upon passing the background noise test, a plurality of hearing screening tones to a user via the headset; determining whether the user has perceived a requisite number of hearing screening tones; switching to an amplification mode based on the determination that the user has perceived less than the requisite number of hearing screening tones; and adjusting a volume of the headset in accordance with hearing capacity of the user; and recommending to the user a comprehensive hearing test based on the hearing screening.

In some examples, the method further includes checking for a source of background noise detected upon failing the background noise test; determining that the background noise detected is capable of being isolated; and performing the hearing screening upon isolating the detected background noise. The method also may include finding a different testing area based on a determination that the background noise detected is not capable of being isolated.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
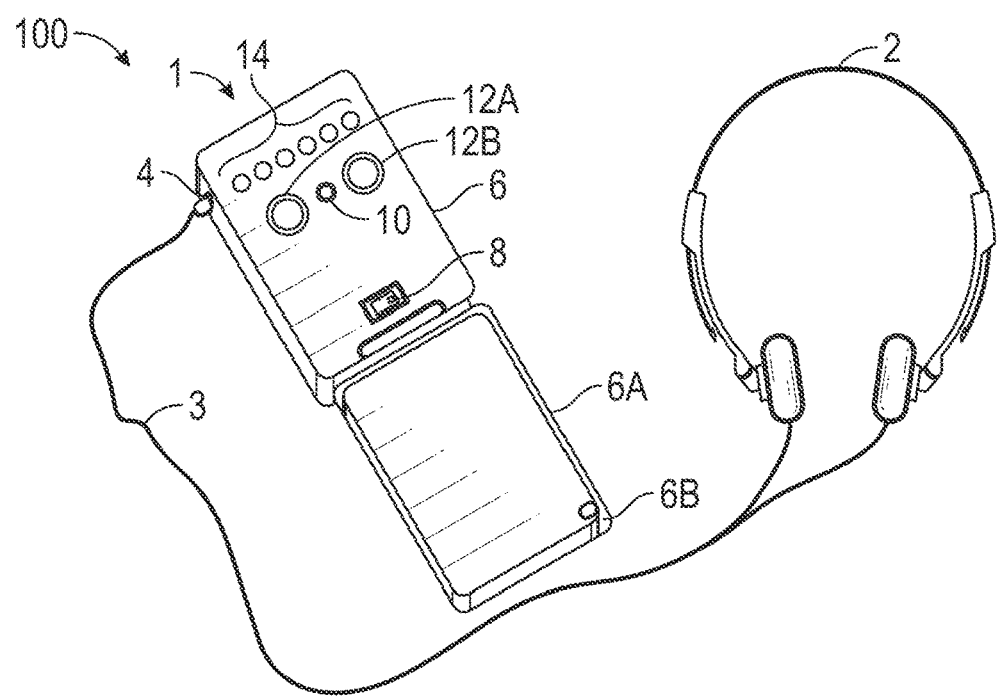
FIG. 1 is a perspective top view of a hearing system according to one particular, non-limiting exemplary embodiment of the disclosed concept.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept will now be described, for purposes of explanation, in connection with numerous specific details in order to provide a thorough understanding of the subject innovation. It will be evident, however, that the disclosed concept can be practiced without these specific details without departing from the spirit and scope of this innovation.

FIG. 1 is a hearing system 100 according to one particular, non-limiting exemplary embodiment of the disclosed concept. The hearing system 100 includes a portable hearing screening and amplification device 1 and a headset 2 that may be coupled to the portable hearing screening and amplification device 1 via a cord 3 and a jack 4 in the portable hearing screening and amplification device 1. The portable hearing screening and amplification device 1 may have a size equal to or less than the size of a hand-held device (e.g., 1.5×5×3 inches or less) so as to fit into a hand of an adult comfortably. The headset 2 may include a low-cost, supra-aural headset or earphones that may fit comfortably over the user's head and ears. While the headset 2 is able to be coupled to the portable hearing screening and amplification device 1 in FIG. 1, the headset 2 also may be or alternatively be wirelessly coupled to the portable hearing screening and amplification device 1, depending on user preferences, circumstances, or needs. The headset 2 may be any inexpensive (e.g., at a cost of less than $10) headset or set of earphones available in the market. The hearing system 100 may operate in two modes: a hearing screening mode and an amplification mode as discussed further in detail below.

Figure 9B:
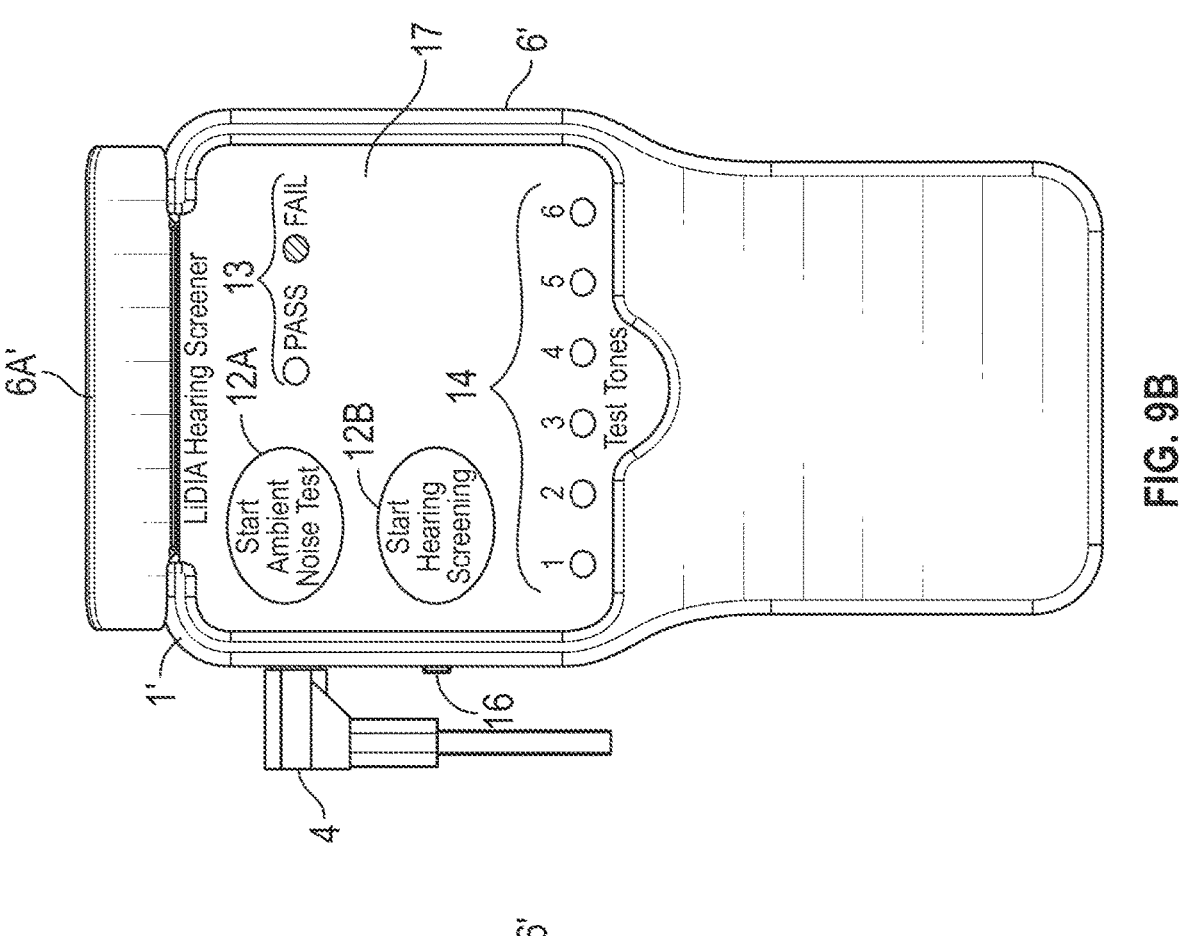
FIGS. 9A-E illustrate an example portable hearing screening and amplification device according to one particular, non-limiting exemplary embodiment of the disclosed concept.

The portable hearing screening and amplification device 1 includes a housing 6 (including housing cover 6A for covering the testing indicators and a protrusion 6B as a latch between the housing cover 6A and the housing 6, a display power switch 8, a status indicator 10, buttons 12A, 12B for hearing screening, and hearing screening indicators 14. When the hearing system 100 is in the hearing screening mode, the housing cover 6A is open and the display power switch 8, the status indicator 10, the buttons 12A, 12B and the hearing screening indicators 14 are visible and accessible to a screener (e.g., a clinician). In some examples, the portable hearing screening and amplification device may not include the display power switch 8 (e.g., the portable hearing screening and amplification device 1' as illustrated in FIGS. 9A-11) since the status indicators 14 may be activated automatically during hearing screening. That is, upon actuation of an ambient noise test (ANT) button 12A, the portable hearing screening and amplification device 1' switches to a hearing screening mode from the amplification mode and the ANT is performed. If the screening location passes or fails the ANT, the corresponding ANT indicator (e.g., without limitation, LEDs) is lit based on a timing algorithm (discussed further in detail with respect to FIG. 10A). If the screening location passes the ANT, the user may actuate the hearing screening button 12B (as shown in FIG. 9B) and the portable hearing screening and amplification device 1' sequentially performs a number of screening tone tests based on a timing algorithm (as discussed further in detail with respect to FIG. 10B), and the status indicators 14 each are structured to be lit when the user has been presented with respective screening tones during a predefined listening time.

The housing cover 6A may contain instructions on its inner surface for conducting a background noise test, hearing screening, or reset operations. When the screener switches from the hearing screening mode to the amplification mode, the housing cover 6A closes and deactivates the display power switch 8, the status indicator 10, buttons 12A, 12B and hearing screening indicators 14. In some examples (e.g., embodiments including the portable hearing screening and amplification device 1' as shown in FIGS. 9A-11), the switching from the hearing screening mode to the amplification mode is implemented via the timing algorithm after the hearing screening. The default mode for the portable hearing screening and amplification device 1' is the amplification mode. The hearing screening mode includes the ambient noise test and screening tone testing. The hearing screening mode is activated by actuating the ambient noise test button 12A. After the hearing screening, the portable hearing screening and amplification device 1' reverts back automatically to the amplification mode after a preset time (e.g., without limitation, seven seconds) based on a timing algorithm. Timing diagrams showing the automatic switching back to the amplification mode is illustrated in FIG. 10B.

Referring back to the portable hearing screening and amplification device 1, upon the completion of the hearing screening, a user (a person being screened, e.g., a patient) can now place the portable hearing screening and amplification device 1 over his or her belt and use the portable hearing screening and amplification 1 coupled to the headset 2 as personal amplification device. The display power switch 8 is structured to switch on and off the power for the hearing screening indicators 14. The status indicator 10 is structured to indicate the status of the portable hearing screening and amplification device 1. For example, if the screener turns off the amplification mode, the status indicator 10 may light or flash in red to indicate a mode change. When the portable hearing screening and amplification device 1 is ready for hearing screening, the status indicator 10 may light in green and the screener may now turn on the hearing screening mode. The buttons 12A, 12B are structured to start a Go/No Go test (i.e., the background noise level test) and to initiate the hearing screening. The hearing screening indicators 14 are structured to sequentially indicate that a testing tone has been transmitted to the headset 2. These are examples of use settings, but this device can be used in any situation where hearing needs to be screened and communication needs to be improved.

Figure 2:
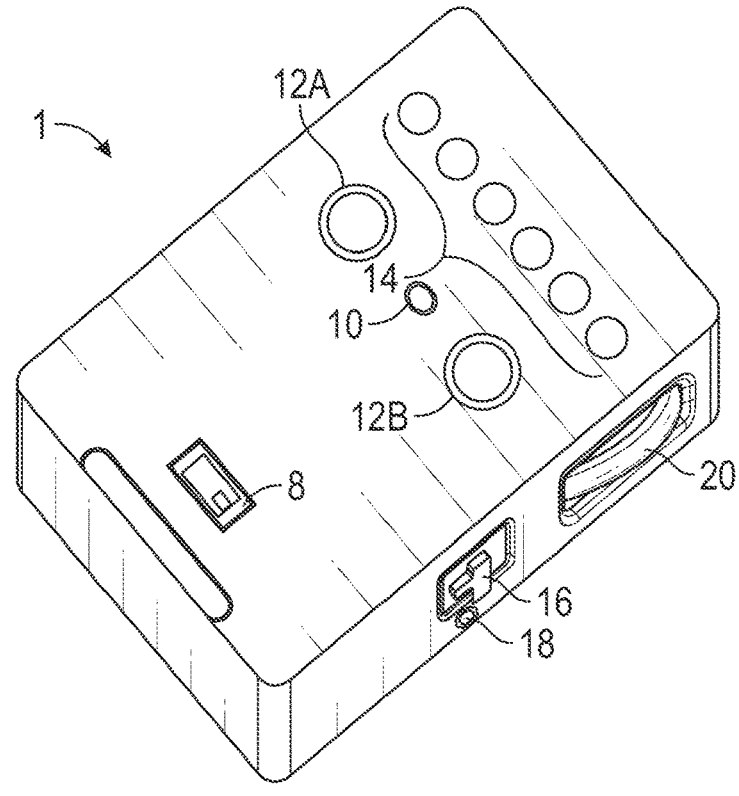
FIG. 2 is a perspective top view of a portable hearing screening and amplification device according to one particular, non-limiting exemplary embodiment, including the various components housed therein.
Figure 3:
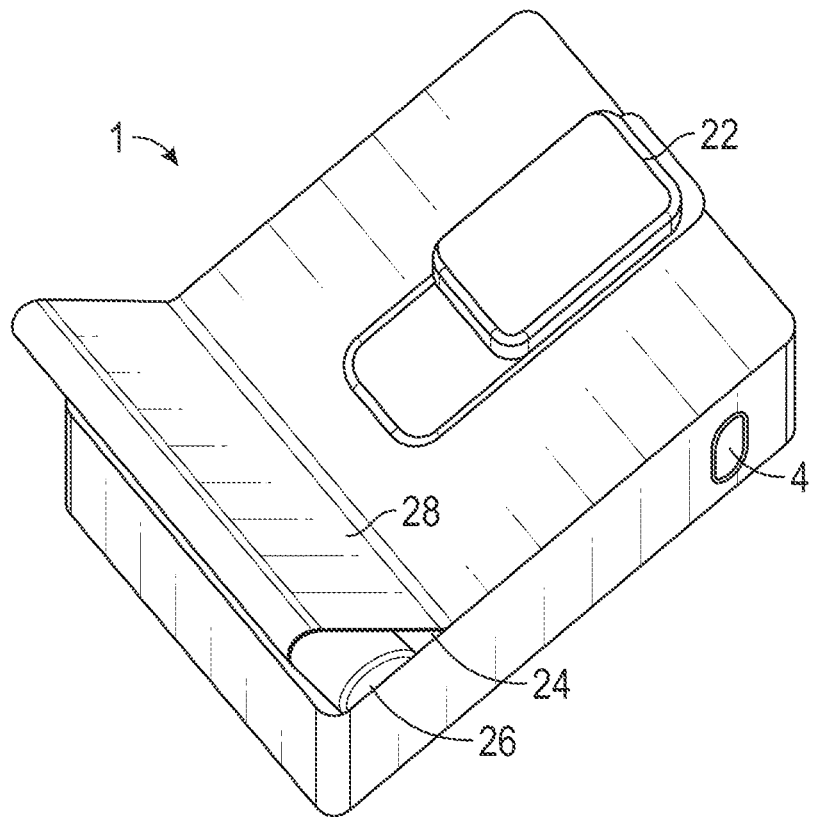
FIG. 3 is a perspective bottom view of a portable hearing screening and amplification device according to one particular, non-limiting exemplary embodiment of the disclosed concept.

FIG. 2 is a perspective top view of a portable hearing screening and amplification device 1 according to one particular, non-limiting exemplary embodiment of the disclosed concept. As shown in FIG. 2, the portable hearing screening and amplification device 1 also includes a power switch 16, a power indicator 18, and a volume adjuster 20. The power switch 16 turns on and off the portable hearing screening and amplification device 1. The power indicator 18 is structured to indicate the power status of the portable hearing screening and amplification device 1 by, e.g., lighting up an LED when the portable hearing screening and amplification device 1 is turned on, or not lighting up when the portable hearing screening and amplification device 1 is turned off or the battery (e.g., battery 26 as shown in FIG. 3) runs out. The volume adjuster (e.g., a potentiometer) 20 is structured to adjust the volume of the sounds fed to the headset 2 when the portable hearing screening and amplification device 1 is being used in the amplification mode. For example, the user (a person being screened for hearing status) may turn up the volume via the volume adjuster 20 if he or she needs the volume increased.

FIG. 3 is a perspective bottom view of a portable hearing screening and amplification device 1 according to one particular, non-limiting exemplary embodiment of the disclosed concept. As shown in FIG. 3, the portable hearing screening and amplification device 1 also includes a clip 22 for clipping the portable hearing screening and amplification device 1 to, e.g., a belt of the user (a person being screened for hearing status), a battery receptacle 24 for a battery 26, and a battery cover 28. The battery receptacle may receive, e.g., two AA batteries in series supplying 3V to the portable hearing screening and amplification device 1. In some examples, three AA batteries may be used for longer battery life supplying 4.5V. The batteries may not be limited to AA batteries. For example, AAA batteries may be used. Further, the batteries may be replaceable or non-replaceable.

Figure 4:
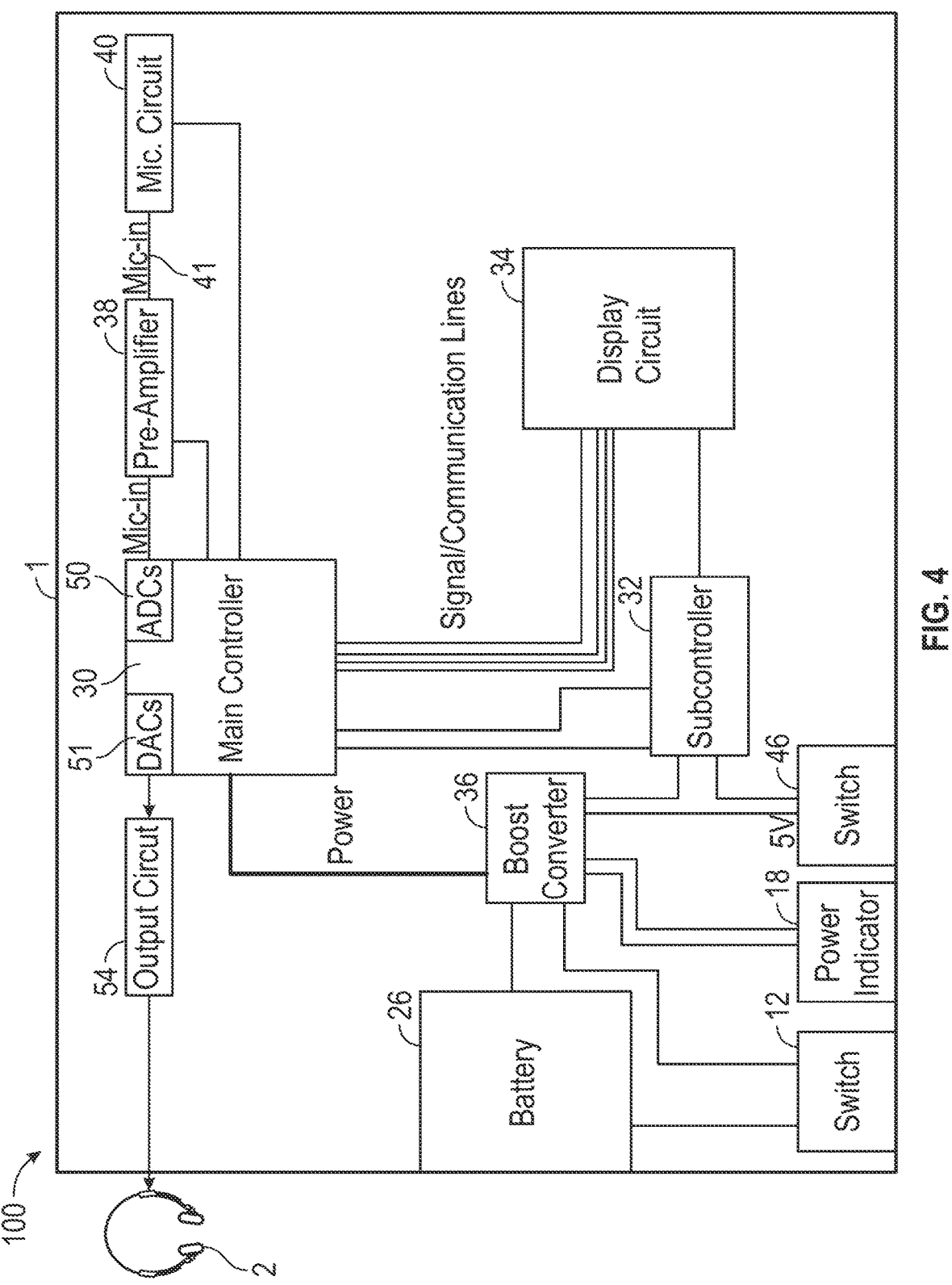
FIG. 4 is a schematic block diagram of a portable hearing screening and amplification device according to one particular, non-limiting exemplary embodiment of the disclosed concept.

FIG. 4 is a schematic block diagram of a hearing system 100 according to one particular, non-limiting exemplary embodiment of the disclosed concept. The hearing system 100 includes a portable hearing screening and amplification device 1 and a headset 2 coupled to the portable hearing screening and amplification device 1. The portable hearing screening and amplification device 1 includes a main controller 30, a subcontroller 32, a display circuit 34, an output circuit (a filter/power amplifier) 54, a battery 26, a boost converter 36, a pre-amplifier 38, a microphone circuit 40 coupled to a mic-in line 41, switches 42, 46 and a power indicator 18. The main controller 30 is structured to control digital signal processing (DSP) and the operations of the display circuit 34, the pre-amplifier 38, and the microphone circuit 40. The main controller 30 may be any type of microcontroller and/or include a memory (not shown) for storing a look-up-table, software application or other applications information. In some examples, the memory may be a separate component. The software (not shown) may be structured to instruct the main controller 30 to perform hearing screening, amplification, or resetting of the portable hearing screening and amplification device 1. In some examples, other logic units (e.g., without limitation, an analog circuitry, FPGAs, microprocessors, digital signal processors, discrete programmable logic devices, integrated programmable logic devices, and custom integrated circuit packages) may be used to perform the functionalities of the main controller 30 and/or the subcontroller 32. The look-up-table (not shown) may include established A-weighted thresholds for the Go/No-Go decision. If the background noise levels are equal or above the established thresholds, then a "No-Go" condition is indicated. If the background noise levels are below the established noise thresholds, then the "Go" condition is indicated. In some examples, the portable hearing screening and amplification device (e.g., the portable hearing screening and amplification device 1' as described with reference to FIGS. 9A-11) may not include the look-up-table since a sound pressure level calibration may be used without using such look-up table. The controller is calibrated to a white noise (uniform power across all audible frequencies) source with a known volume, establishing one level in dB SPL threshold (e.g., without limitation, 49 dB SPL) that dictates the Go/No Go recommendation. During the ambient noise test, any sound picked up by the microphone above the established dB SPL threshold triggers a failed ambient noise test.

The thresholds included in the look-up-table were established by performing a large number of sound recordings that were collected using a microphone and data acquisition in every day medical and geriatric environments to obtain data representative of typical background noise in these settings. In addition, the sound recordings may use a free-field Larson Davis System 824 Sound Level meter (SLM) to measure environmental noise levels. Typical settings include outpatient exam rooms, inpatient settings, independent living facilities, assisted/personal care facilities, skilled nursing facilities, and emergency room environments, etc. Each collected data sample may then be cut into useable clips with low variability (where sound level is fairly steady, e.g., without doors slamming, human speech, etc.), scaled to be amplified, and looped to form WAV files for playback in an audiometric or sound-proof booth for establishing subjective tone recognition thresholds in the presence of the recorded background noise. Spectral analysis may be performed on each clip to examine frequency content within the range of speech, which could interfere with speech communication. Once the Go/No-Go thresholds were established with regards to the ability for human subjects to perceive a 35 dB HL tone across frequencies, they are stored as a table look up for each frequency tone used for the hearing screening. The thresholds may be A-weighted or unweighted to be compared with respective A-weighted or unweighted measured examining room sounds levels.

The main controller 30 is structured to output a hearing screening signal through digital to analog converters 51 to the headset 2. The controller, in conjunction with subcontroller 32 receives user input from button 12A to initiate the background noise test and button 12B to initiate the hearing screening test. The two controllers also indicate test status via the hearing screening indicators 14 and background noise test status indicator 10. In some examples, the main controller 30 and the subcontroller 32 may be merged into one controller (e.g., without limitation, one microcontroller) performing each and every function of the main and subcontrollers. Alternately, the functions could for example also be performed using an application specific integrated circuit (ASIC), analog circuitry (e.g., using A-weighting and bandpass filters, squaring circuitry, exponential averaging circuitry, peak detectors, comparators, etc.), an FPGA, or digital logic.

The display circuit 34 may be structured to include hearing screening indicators 14 and the status indicator 10. The display circuit 34 also may include: a first indicator for status of background noise check, a second indicator for status of hearing screening, a background noise check activator, a hearing screening activator, a volume adjuster structured to change from hearing screening to personal amplification and adjust volume of the portable hearing screening and amplification device 1. In some examples, there may be separate components that perform a mode change and volume adjustment. The boost converter 36 is structured to increase the voltage from e.g., 3V to 5V or other appropriate voltage for the electronics hardware. In some examples, the boost converter 36 may not be included as the power boosting for the hardware may not be necessary.

The microphone circuit 40 provides voltage to the microphone element and routes the microphone signal to the pre-amplifier. Pre-amplifier 38 converts the charge output of the microphone into a voltage that is proportional to the measured acoustic pressure and provides gain to the microphone signal. The microphone circuit 40 may include a microphone, for example a MEMS or piezoelectric microphone element, a DC operating voltage, and conditioning electronics structured to detect any sound, background (ambient) noises, e.g., background noise testing. From there, the microphone signal is further conditioned and amplified by the pre-amplifier 38 before being sampled using and analog to digital converter (ADC) 50 so that controller 30 may use the digital representation of the Mic-In signal. A digital gain may be applied to the Mic-In signal inside controller 30, for example to apply a calibration factor to the signal from microphone circuit 38. If the portable hearing screening and amplification device 1 is in background noise level checking mode, then the background noise level is computed from the Mic-In signal by the controller 30. If the hearing device 1 is in amplification mode, a digital gain may be applied to the Mic-In signal which is then coupled to the digital to analog converters (DAC) 51. In some examples (e.g., the embodiments including the portable hearing screening and amplification device 1' as described with reference to FIGS. 9A-11), the microphone circuit 40 may include a digital microphone with the built-in functions (e.g., without limitation, detecting background noises, computing the background noise levels, detecting sound for amplification), which may be programmable. Further, the digital microphone allows the portable hearing screening and amplification device 1' to have programable equalization. As such, frequency and volume adjuster-based gain settings may be applied.

The DAC 51 is coupled to the output circuit 54, which is a filter/power amplifier, so that the signal can be frequency shaped and have its power increased sufficiently to drive the speakers of the headset. In some examples, filter/power amplifier 54 may include separate analog filter and power amplifier that are independent of controller 30. For example, the analog filter may be a low pass reconstruction filter for the DAC 51. The output for filter/power amplifier 54 is coupled to the headset 2. The switch 42 is placed between the battery 26 and the boost converter 36 and structured to prevent the boost converter 36 from supplying power to the portable hearing screening and amplification device 1 when the portable hearing screening and amplification device 1 is not being used. Upon the closing of switch 42, the 3V power is routed from the switch 42 to the boost converter 36 and grounded. The switch 46 is structured to feed the power from the boost converter 36 to subcontroller 32. While FIG. 4 shows a number of switches (e.g., power switch 42 to turn on the portable hearing screening and amplification device 1, power switch 46 to activate background noise test, etc.), it will be understood that functionalities of these switches may be performed by one component (e.g., controllable via software) in other embodiments.

Display circuit 34 is comprised of status indicator 10, buttons 12A and 12B, display power switch 8, hearing screening indicators 14 and status indicator 10, which are coupled to either main controller 30 or subcontroller 34. The connections between the main controller 30 including DSP logic coupled to communication pins, for example GPIO (general-purpose input/output) pins, the subcontroller 32 and display circuit 34. The mode switch attached to potentiometer 20 is structured to enable or disable the amplification mode of the hearing system 100. By scrolling the potentiometer 20 (e.g., turning or moving the potentiometer 16 until the integrated mode switch (not shown) clicks on), the amplification mode may be enabled. When the mode switch is off, the amplification mode is disabled. When the mode switch attached to potentiometer 20 is in the off position and the main power switch 42 is on, the DSP may automatically assume the Hearing Screening Mode and wait for the environmental switch 12A (a background noise test button) to be pressed by a screener (e.g., without limitation, a clinician, an examiner). When the environmental switch 12A is pressed, it triggers the start of the background noise level test, which includes a timer (not shown) and that determines the duration of the background noise test. If the background noise is below predetermined levels, the test passes, and then a second timer may start, waiting for the screening button 12B to be pressed. If the hearing screening button 12B has not been pushed within a certain amount of time determined by the second timer, the background level test must be run again by pressing button 12A before the hearing screening can be conducted.

For example, when the status indicator light 10 is lit in green, the portable hearing screening and amplification device 1 is ready for hearing screening. When the environmental switch 12A is pressed, a flag is set HIGH indicating to main controller 30 to initiate the background noise level check. The portable hearing screening and amplification device 1 goes into a loop for, e.g., 5 seconds while the DSP measures the background noise level. If the noise level does not exceed the preestablished thresholds, then the Go status is indicated. Otherwise, if the background level does exceed the thresholds, then a No-Go status is indicated. If the system 100 fails the sound level test, the DSP resets and the status indicator light 10 may indicate failure of the test (No Go) and return to the original ready state. If the peak sound level did not exceed its threshold, the status indicator light 10 is set to green. The system 100 may enter, e.g., a while loop for five seconds. If the hearing screening button 12B is not pressed, the while loop may run out and the portable hearing screening and amplification device 1 may indicate No-Go for, e.g., three seconds. If the hearing screening button 12B is pressed, a flag may be set to HIGH, signaling the main controller 30 to initialize the hearing screening function. The display circuit 34 outputs an indicator as a respective hearing screening tone is played into the left or right ear of the headset 2. For example, as the first tone is played into the left ear of the headset 2, the first green light of hearing screening indicators 14 may flash; as the second tone is played, the first indicator light may remain solid green while the second indicator light flashes; and so on until three different tones are played back to the patient for both ears. Upon completion of the hearing screening, the DSP and the main controller 30 return to their initial state.

Figure 5:
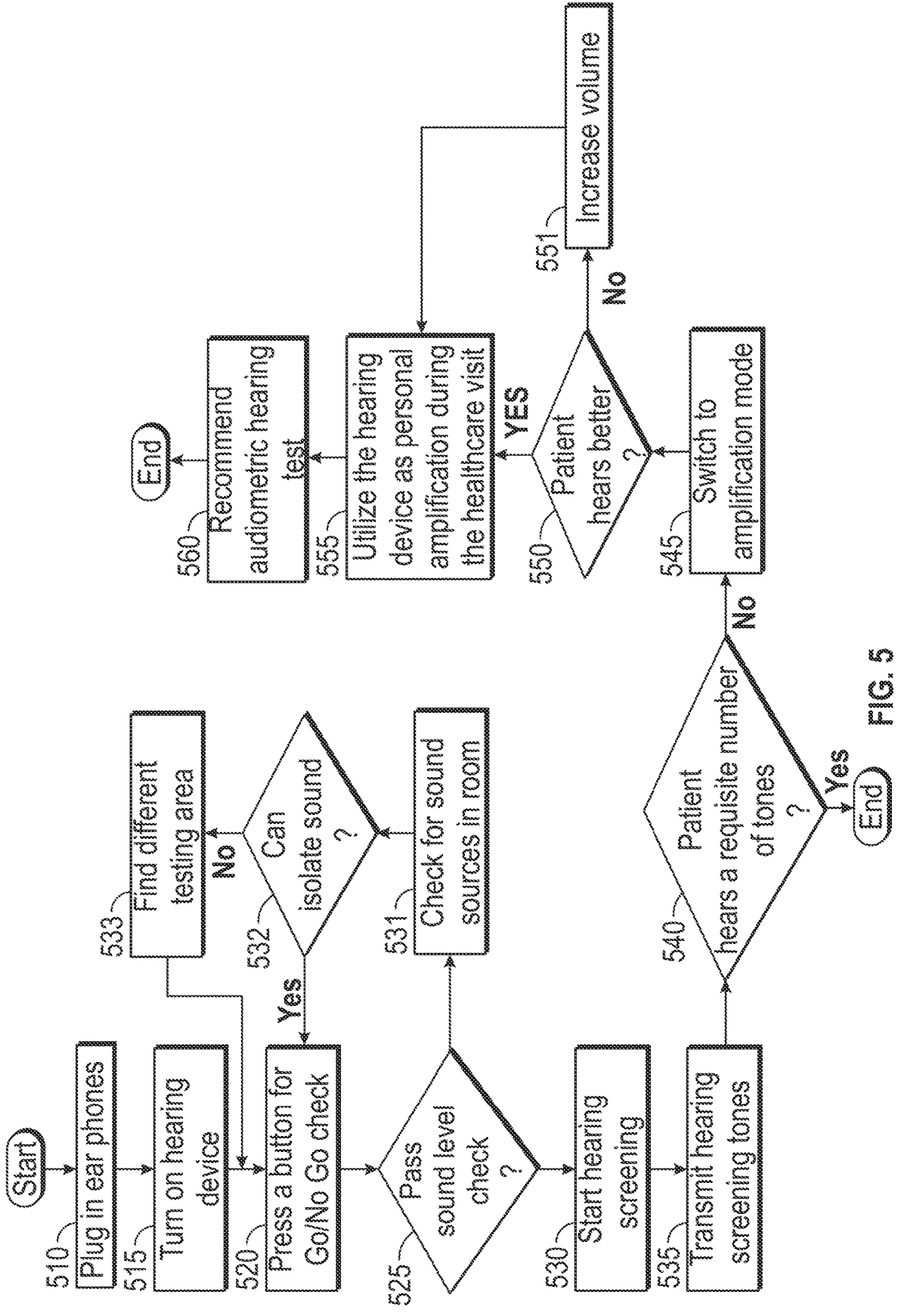
FIG. 5 is a flowchart for a method of hearing screening and amplification according to one particular, non-limiting exemplary embodiment of the disclosed concept.

FIG. 5 is a flowchart for a method 500 of hearing screening and personal amplification according to non-limiting exemplary embodiments of the disclosed concept. The method 500 may be performed using a portable hearing screening and amplification device 1 as described with reference to FIGS. 1-4 and portable hearing screening and amplification device 1' as described with reference to FIGS. 9A-11.

At 510, a screener couples ear phones into a portable hearing screening and amplification device for hearing screening. A screener may be a clinician, a health aid, etc., who may have received a minimal training in how to use the portable hearing screening and amplification device 1, e.g., how to plug in the ear phones, turn on/off the portable hearing screening and amplification device, switch to amplification mode, etc.). The screener hands the ear phones to a user (a person being screened, e.g., a patient). The user then places the ear phones to his or her ears or the screener may place the ear phones. The ear phones may be any comfortable, inexpensive ear phones or headsets available in the market. The hearing screening may take place at a medical visit (e.g., without limitation, a healthcare visit, emergency room visit, a routine check-up, inpatient stay, enrollment in senior living).

At 515, the screener turns on the portable hearing screening and amplification device for hearing screening. The portable hearing screening and amplification device may then enter into a waiting mode.

At 520, the screener presses a button on the portable hearing screening and amplification device for Go/No Go check for a sound level check (e.g., background noise check) of a testing area (a screening location), e.g., without limitation, a healthcare visit room, a hearing screening room. A status indicator light may inform the screener of the system power status and readiness to conduct the background noise check. The sound level check is performed to determine whether the background noise of the testing area is at a level such that the hearing screening may be performed effectively and successfully.

At 525, the screener determines whether the healthcare visit room has passed the sound level check, and thus, it is Go for the hearing screening. A status indicator light may inform the screener of the system power status and readiness to conduct the background noise check. Signals measured by a microphone within the portable hearing screening and amplification device are processed to form A-weighted sound levels and compared to a predefined maximum permissible sound pressure level. That is, the background noise level should be low enough to allow for hearing screening, e.g., a 35 $dB_{HL}$ hearing loss to be detected in the patient at each of the desired frequencies (e.g., 1 kHz, 2 kHz, 4 kHz, etc.). It will be understood that the hearing loss screening level may be other than 35 $dB_{HL}$. The frequencies and thresholds were pre-established using audiometric testing in various health care settings to establish the frequencies and level required to meet the World Health Organization hearing screening standards for impactful hearing loss. If the noise level required for accurate screening is exceeded, the portable hearing screening and amplification device will indicate that the background noise test failed (e.g., by lighting a red LED) and prevent the hearing screening from being performed. Upon determination of such failure, the method proceeds to 531. At 531, the screener checks for sound sources in the room. It may be possible to reduce excessive background noise by eliminating noise sources near the user or by moving to a quieter location. Upon determining the sound sources, at 532 the screener determines whether he or she can isolate the sound so that the background noise may be contained, and hearing screening performed. For example, if a voice of a person speaking in the background is detected, the screener may request the person to remain quiet during background noise test and the hearing screening. If the screener can isolate the sound sources, the method returns to 520. If the screener cannot isolate the sound sources, at 533 he or she finds a different testing area (e.g., a different healthcare visit room) and upon finding such area the method returns to 520. If, at 525, it is determined that the testing area has passed the sound level check (i.e., the background noise level is within the predefined maximum permissible sound pressure level), the method continues to 530. If the testing area passes the background noise test, the portable hearing screening and amplification device may indicate (e.g., by lighting a green LED) that the testing area has passed the background noise test. A number of indicators may be more than two (e.g., two LEDs) depending on circumstances and needs.

At 530, the screener starts hearing screening by pressing a button on the portable hearing screening and amplification device. Alternatively, the portable hearing screening and amplification device (e.g., a software within the portable hearing screening and amplification device) may start the hearing screening after a wait period (e.g., 5 seconds) to avoid noise level changes in the room from interfering with the hearing screening.

At 535, the portable hearing screening and amplification device transmits hearing screening tones. A number of hearing screening tones transmitted may be, e.g., six tones. That is, three sequential tones are played in each ear of the patient. The tones may span across three octaves and within a primary hearing range ((250-4,000 Hz), e.g., the upper part of the primary hearing range (e.g., 1 kHz, 2 kHz, 4 kHz), where hearing loss is typically prevalent, leading to communication difficulties. Tone amplitudes may be set to correspond to the threshold of impactful hearing loss threshold (i.e., 35 $dB_{HL}$). The portable hearing screening and amplification device may include six indicators (e.g., six LEDs) and the screener may see the six indicators light up in sequence, corresponding to the playback of the six tones. The number of indicators may be more than six depending on a number of hearing screening tones tested, the circumstances and need. The hearing screening tones are transmitted to the headsets, which the user is wearing, in an interval of, e.g., without limitation, five seconds so as to allow the user sufficient time to perceive the tone. The number of seconds in the interval varies so as not to allow the user to recognize a pattern and respond inaccurately.

At 540, the screener determines whether the user hears a requisite number of tones (e.g., 5 tones). After playback completion, the user may be instructed to report how many tones he or she heard during the hearing screening. For example, if the user has heard fewer than five tones, the user is considered to have a high probability of impactful hearing loss. If the user indicates that they heard 5 or 6 tones, thereby indicating no disabling hearing loss, the screener may turn off the portable hearing screening and amplification device, remove the headphones from the user, and proceed with the healthcare visit. If the user has not heard the requisite number of tones, then the method proceeds to 545.

Figure 10A:
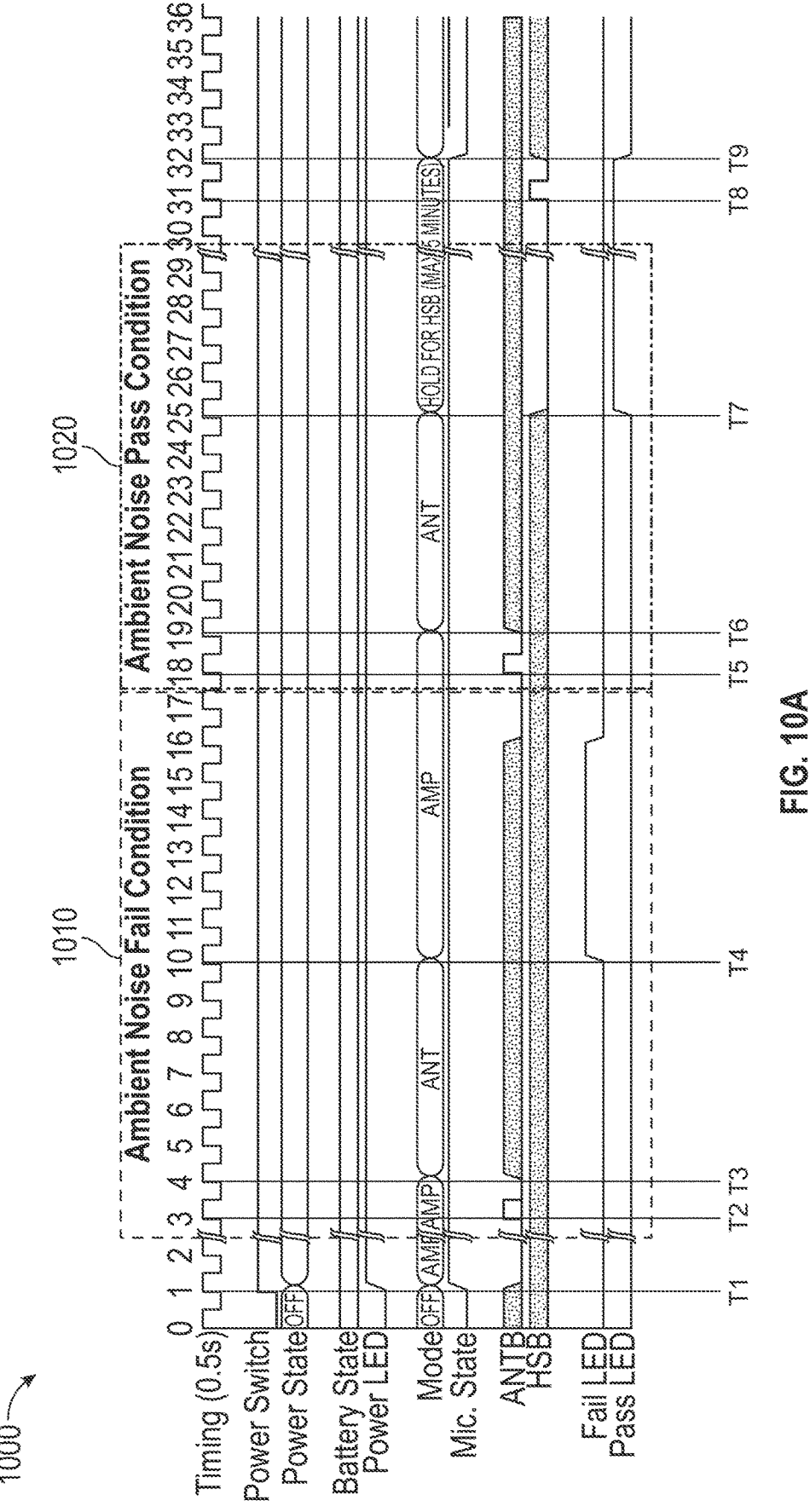
FIGS. 10A-B illustrate a timing diagram of a portable hearing screening and amplification device according to one particular, non-limiting exemplary embodiment of the disclosed concept.

At 545, the personal hearing screening and amplification device is switched from the hearing screening mode to the amplification mode. In the example using the personal hearing screening and amplification device 1, the screener switches the portable hearing screening and amplification device from a hearing screening mode to an amplification mode via, e.g., turning a volume adjuster of the portable hearing screening and amplification device 1. In the examples using the portable hearing screening and amplification device 1', the switching from the hearing screening mode to the amplification mode is automatic based on a timing algorithm as shown in FIG. 10A.

At 550, the screener determines whether the user can hear better in the amplification mode. The portable hearing screening and amplification device may have a knob (e.g., a potentiometer) or other means to allow the user to adjust the volume to his or her comfort level. The portable hearing screening and amplification device also may include a body clip to allow the user to use the device hands-free. If the user cannot hear better, at 551 the user may increase the volume of the portable hearing screening and amplification device in the amplification mode. Upon increasing the volume, at 555 the user utilizes the portable hearing screening and amplification device as an amplification device during the healthcare visit.

At 560, the screener communicates the hearing screening results to the managing health care provider who may recommend referral for a comprehensive hearing test after this healthcare visit. The user may keep the portable hearing screening and amplification device with the headset for everyday use until he or she obtains a more individualized hearing solution after audiometric testing depending on the protocol of the particular health care site. Alternatively, the device can be cleaned appropriately and used with the next patient. The portable hearing screening and amplification device may be a size equal to or less than a size of a hand-held device (e.g., having 3-inch width, 5-inch length, and 1.5-inch depth or less dimensions). The portable hearing screening and amplification device also may include a battery slot for easily replacing batteries. Standard battery sizes (e.g., AA, AAA, etc.) may be used. For example, the portable hearing screening and amplification device 1 as described with reference to FIGS. 1-4 may use, e.g., without limitation, two AA batteries in series supplying 3V to the portable hearing screening and amplification device 1. In another example, the portable hearing screening and amplification device 1' as described with reference to FIGS. 9A-11 may use, e.g., without limitation, three AA batteries supplying 4.5V to the portable hearing screening and amplification device 1'. The portable hearing screening and amplification device also may be capable of being coupled to a wireless headset in accordance with the user preference.

Figure 6:
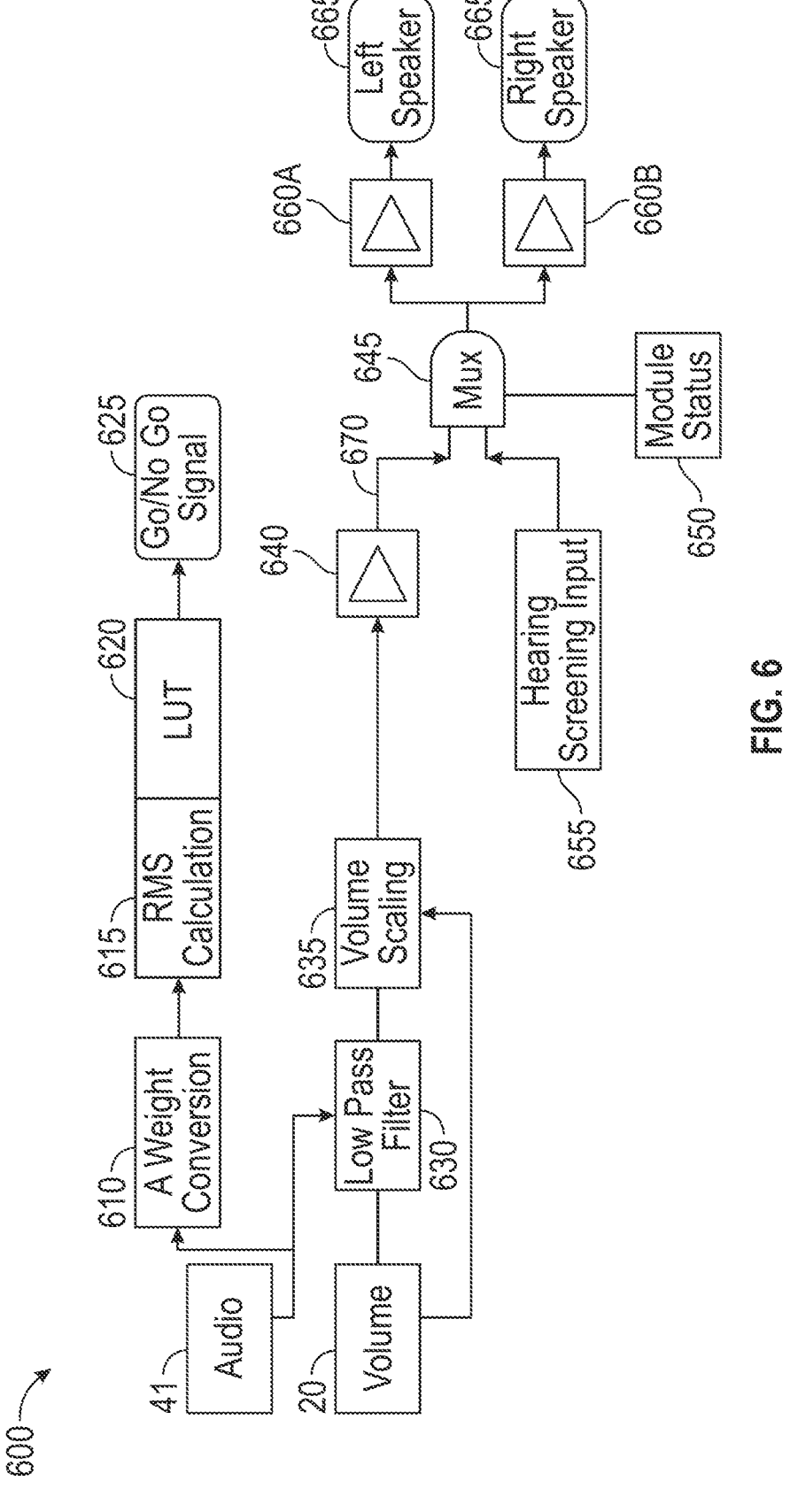
FIG. 6 is a flow diagram of background noise test and amplification according to one particular, non-limiting exemplary embodiment of the disclosed concept.

FIG. 6 is a flow diagram of a background noise test, personal amplification, and hearing screening 600 using a personal hearing screening and amplification device 1, 1' according to non-limiting exemplary embodiments of the disclosed concept. A microphone-in line (audio-line in) 41 may be split into two paths: one for checking the background noise level and one for the amplification mode and hearing screening mode. Mode selector 650 can control multiplexer 645 to determine which audio signal is fed to power amplifiers 660A-B and connected to the headphones 665A-B. Alternately, in hearing amplification mode, a single amplifier 660 may amplify a single channel (mono) signal that is applied to both headphone speakers 665. During the hearing screening mode, the audio-in signal 41 from the microphone 40 (FIG. 4), microphone pre-amplifier 38, and analog to digital converter or ADC (not shown) may be used for the background noise test, and the audio in 41 is A-weighted by A-weighting conversion filter 610. The A-weighting filter may be applied in the time or frequency domain or it could be an analog filter placed after microphone preamplifier 38. For example, the input signal 41 from the microphone 40 may be sent through an A-weighting filter constructed in blocks in the software (e.g., a digital filter or bank of smaller filters in series or parallel designed using SigmaStudio® by Analog Devices, Inc.) with coefficients adjusted to match a discretized version of the Laplace domain transfer function Eq. 1 as shown below:

$$HA(s) = \frac{k_A s^A}{(s+1.29.4)^2(s+676.7)^2(s+4636)(s+76655)^2} \qquad \text{EQ. 1}$$

where $k_A$ is a constant that normalizes the gain to unity at frequency 1 kHz and is equal to $7.39705 \times 10^9$. By A-weighting the response, low and high frequencies are attenuated to mirror human perception. Alternately, unweighted sound pressure levels could also be used if they are compared against unweighted Go/No-Go noise thresholds. In either case, the signals undergo Go (the established background noise thresholds not being exceeded) or No-Go (fail the threshold sound pressure level due to background noise level limits being exceeded) 625. A microphone used for collecting the background noises is calibrated to collect an output voltage of a microphone circuit for background noise test thresholds. The background noise may be collected from a plurality of environments, e.g., outpatient exam rooms, inpatient settings, independent living facilities, assisted/personal care facilities, skilled nursing facilities, and emergency room environments, etc. The background noise may then be sampled for, e.g., five seconds; root mean square value is calculated 615. In the examples using the portable hearing screening and amplification device 1 as described with reference to FIGS. 1-4, a maximum value may be used as an input to be fed into a look-up table 620 including predetermined voltage levels that are associated with the background noise threshold limits. The look-up table 620 may be a digital filter bank and may be implemented using analog devices software or any other software. In the examples using the portable hearing screening and amplification device 1' as described with reference to FIGS. 9A-11, a sound pressure level calibration may be used without using a look-up table 620. The controller is calibrated to a white noise (uniform power across all audible frequencies) source with a known volume, establishing one dB SPL threshold. During the background noise test, any sound picked up by the microphone above a sound pressure level threshold (e.g., without limitation, 49 dB SPL) triggers a failed ambient noise test. For the hearing screening mode, the output level of the digital to analog converters (DACs, not shown) in the hearing screening input to the headset 2 is adjusted to the appropriate test levels using an internal software gain.

During the amplification mode the audio signal 41 may be sent through a low pass filter 630 and then scaled via the volume adjuster 20. For example, the functions of volume adjuster 20 and volume scaling 635 are combined into a single device, such as logarithmically tapered volume potentiometer that provides variable resistance between the audio signal and gain block 640. In another example, volume adjuster 20 could be buttons, digital potentiometer, joystick, slider, or similar digital or analog input device that controls a digital gain volume scaling circuit 635. After volume scaling 635 the audio signal may go through a fixed preamplifier gain 640 to create the microphone signal input 670 before entering stereo multiplexer (mux) 645. From there, the signal may go through a digital gain, digital to analog converter (DAC), and then to the power amplifiers 660. From there, the amplified signals may be connected to the headset, e.g., stereo audio jack 4 to which speakers 665 are connected. In yet another example, the gain may be adjusted automatically by an analog or digital circuit to provide output levels above the ambient noise levels, e.g., at a predefined level above the ambient noise levels. In yet another example, analog or digital electronics or software components may be used to adjust the output levels of the device, which may be used to prevent damage to a user's hearing.

Figure 7:
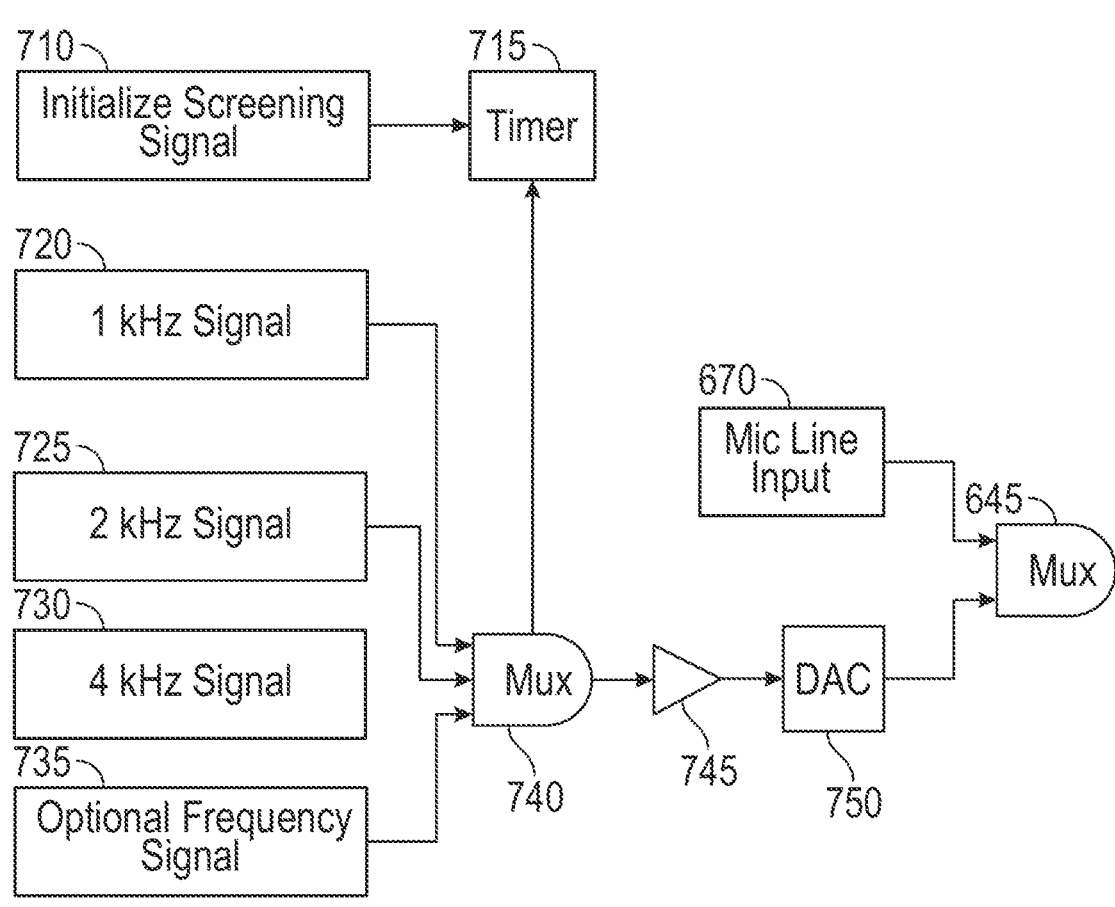
FIG. 7 is a flowchart of hearing screening according to one particular non-limiting exemplary embodiment of the disclosed concept.

For the amplifier mode, the default microphone output from the analog to digital converters (ADCs, not shown) may need to be adjusted to provide appropriate voltage levels for the amplifiers 660. A gain block (a set value) 640 may be added, the output of which is microphone signal 670 which in turn connects to multiplexer 645. One or more additional gain blocks may be added between each frequency tone block (e.g., frequency blocks 720, 725, 730 and 735 as shown in FIG. 7) and the mux 645. The mode of operation determines the state of mux 645. Upon completion of the background noise test the timers (as shown in FIG. 7) may all be reset and the portable hearing screening and amplification device 1 may wait for further input from the screener. The output tone may be passed first to one path associated with the left amplifier 660A and speaker of the headphones 665A and then a second path associated with the right amplifier 660B and speaker of the headphones 665B.

FIG. 7 shows a flow diagram of hearing screening 700 using a portable hearing screening and amplification device (e.g., a portable hearing screening and amplification device 1 as described with reference to FIGS. 1-4 and a portable hearing screening and amplification device 1' as described with reference to FIGS. 9A-11) according to non-limiting embodiments of the disclosed concept. When the portable hearing screening and amplification device has entered the hearing screening mode as a result of the hearing screening signal 710, the hearing system may initialize one or more timers 715. These timers 715 may produce HIGH signals that are fed to an adder block (not shown) that may indicate to the multiplexer (mux) 740 which signal should be passed through to gain 745. FIG. 7 shows 1 kHz 720, 2 kHz 725, 4 kHz 730, and any optional frequency signals (such as in the 250 and/or 500 Hz) 735 connected to the inputs of the mux 740 to create hearing screening input 655. The output of the mux 740 goes to digital software gain 745 and then to the digital to analog converter (DAC) 750. Alternately, each input signal 720, 725, 730, 735 may have its own fixed digital gain (not shown) before multiplexer 740 in lieu or in addition to gain 745. The output of the DAC 750 connects to mux 645 which selects whether the hearing screening input 655 or the microphone signal input 670 from gain 640 is connected to power amplifiers 660 and speakers 665. However, this is for illustrative purposes only and the signals may vary depending on the circumstances and need.

Figure 8:
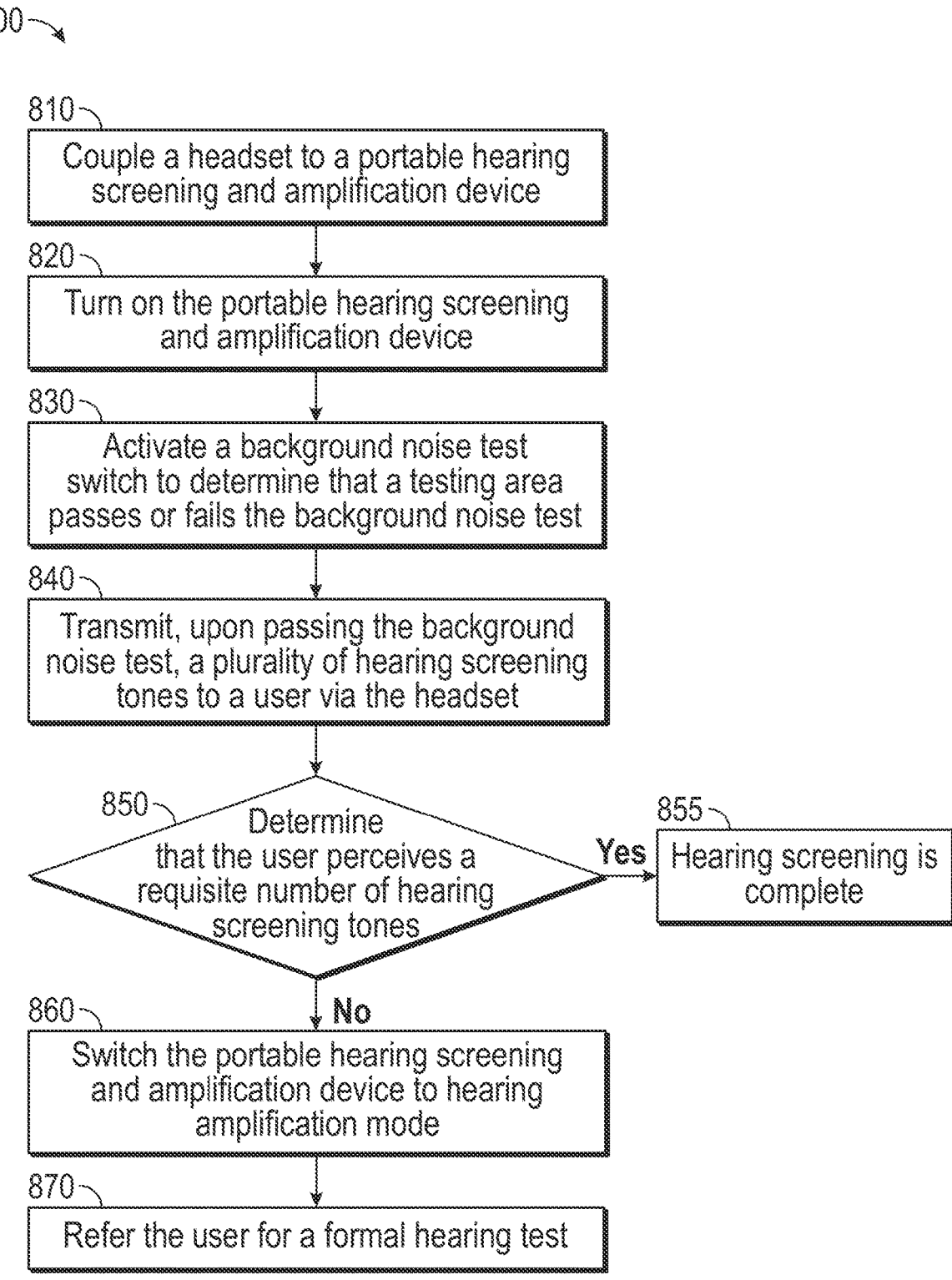
FIG. 8 is a flowchart for a method of hearing screening and amplification according to one particular, non-limiting exemplary embodiment of the disclosed concept.

FIG. 8 is a flow chart for a method 800 for hearing screening according to non-limiting embodiments of the disclosed concept. The method 800 may be performed by a portable hearing screening and amplification device (e.g., the portable hearing screening device 1 as described with reference to FIGS. 1-4 and a portable hearing screening device 1' as described with reference to FIGS. 9A-11 and/or components therein.

At 810, a screener may couple the headset to the portable hearing screening and amplification device. A user (a person being screened for hearing status, e.g., patient) may place the headset over his or her ears for the hearing screening.

At 820, the screener may turn on the portable hearing screening and amplification device.

At 830, the screener may activate a background noise test switch to determine whether a testing area passes or fails the background noise test. If the testing area (the screening location) fails the background noise test, the screener may check for a source of background noise detected and determine whether the background noise detected is capable of being isolated. For example, if a person was speaking in the background, the screener may request the person to pause speaking during the background noise test and the hearing screening. If the background noise detected can be isolated, the screener may reactivate the background noise test switch upon isolating the detected background noise. If the background noise detected cannot be isolated, the screener may find a different screening location and perform the background noise test at the different screening location.

At 840, the screener may transmit, upon passing the background noise test, a plurality of hearing screening tones to the user via the headset.

At 850, the screener may determine whether the user perceives a requisite number of hearing screening tones. For example, the user may receive six hearing screening tones within the primary hearing tones (e.g., 1 kHz, 2 kHz, 4 kHz, etc.). The requisite number of hearing screening tones in such example may be at least five out of the six hearing screening tones. If the user perceives the requisite number of hearing tones, at 855 the user has passed the hearing screening and the hearing screening is complete. If the user does not perceive the requisite number of the hearing screening tones, at 860 the user fails the hearing screening and the portable hearing screening and amplification device switches from the hearing screening mode to the amplification mode. In the example using the personal hearing screening and amplification device 1, the screener switches the portable hearing screening and amplification device from a hearing screening mode to an amplification mode via, e.g., turning a volume adjuster of the portable hearing screening and amplification device 1. In the examples using the portable hearing screening and amplification device 1', the switching from the hearing screening mode to the amplification mode is automatic based on a timing algorithm as shown in FIG. 10B.

At 870, the screener may refer the user for a formal hearing test.

Figure 9A:
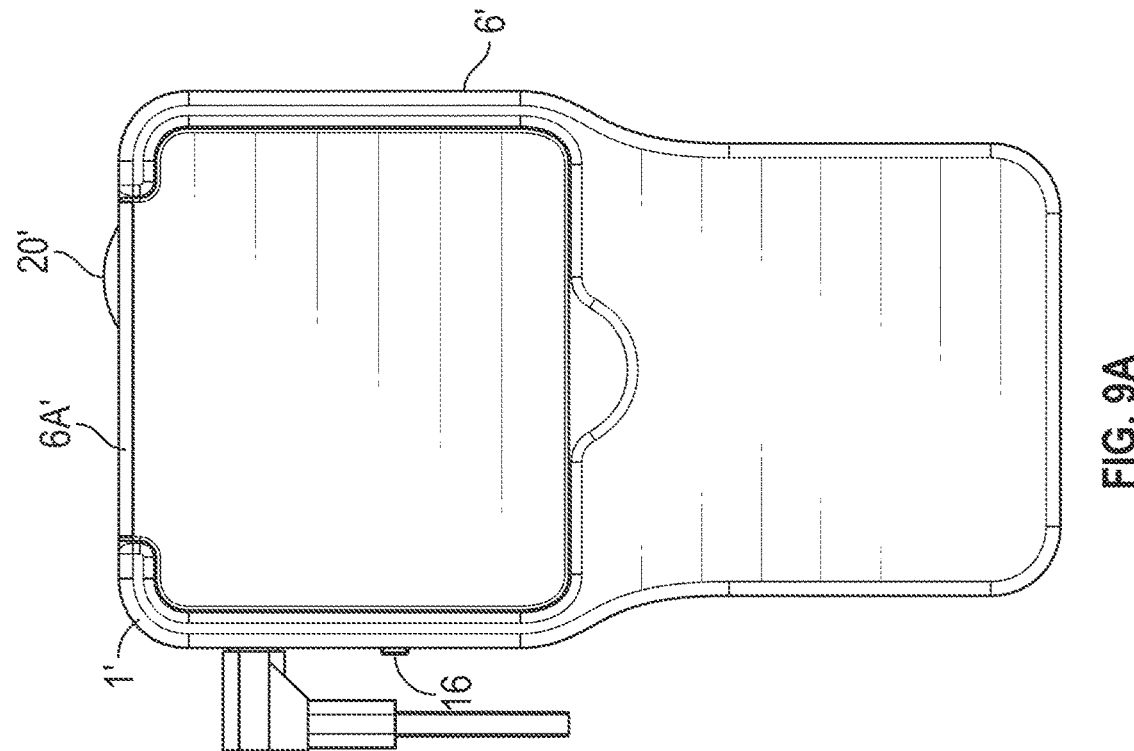
Figure 9C:
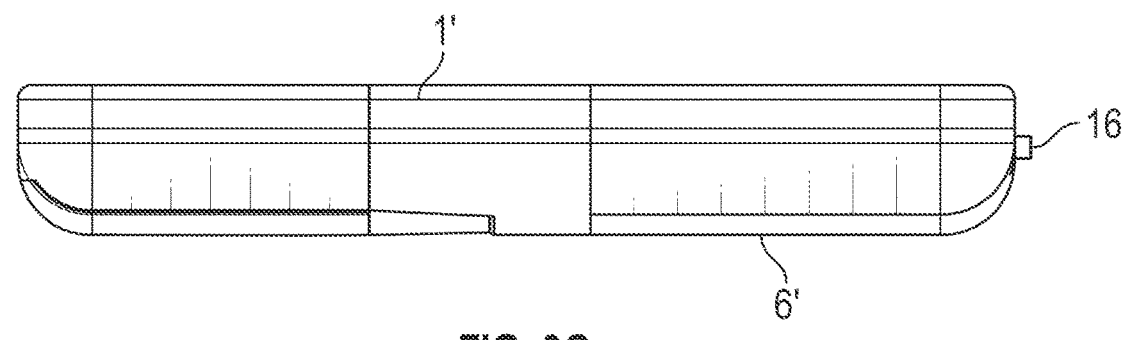
Figure 9D:
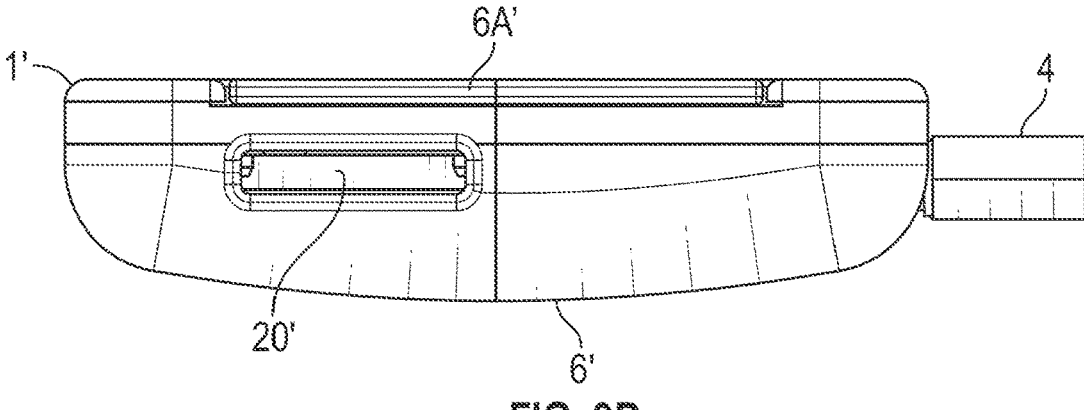
Figure 9E:
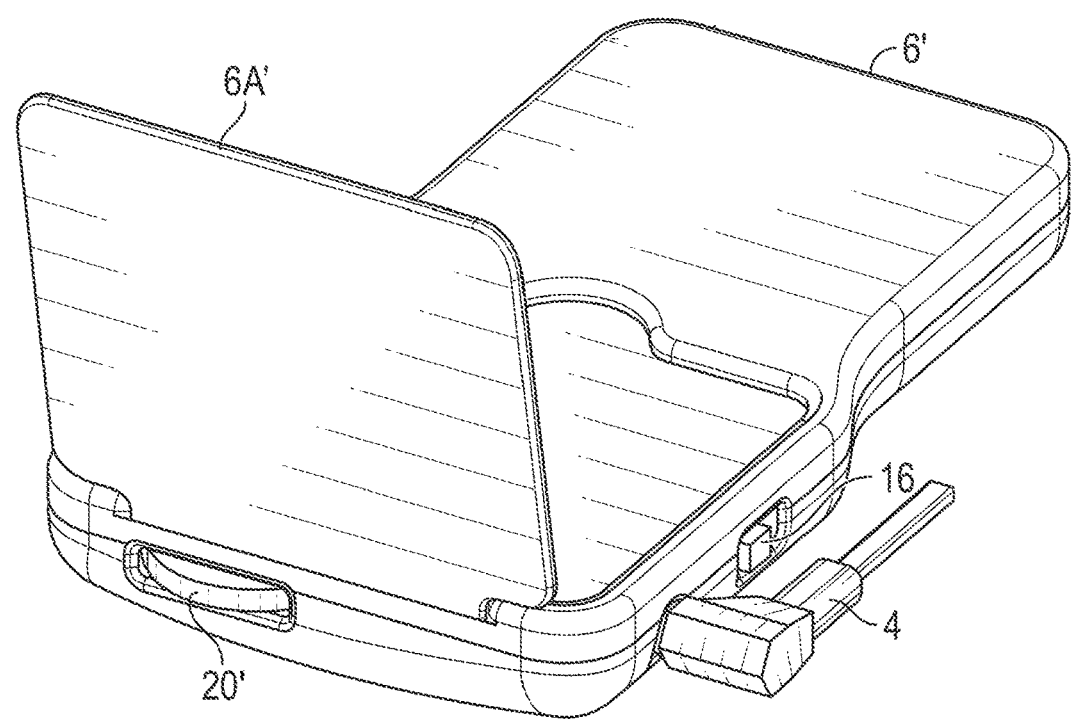
Figure 10B:
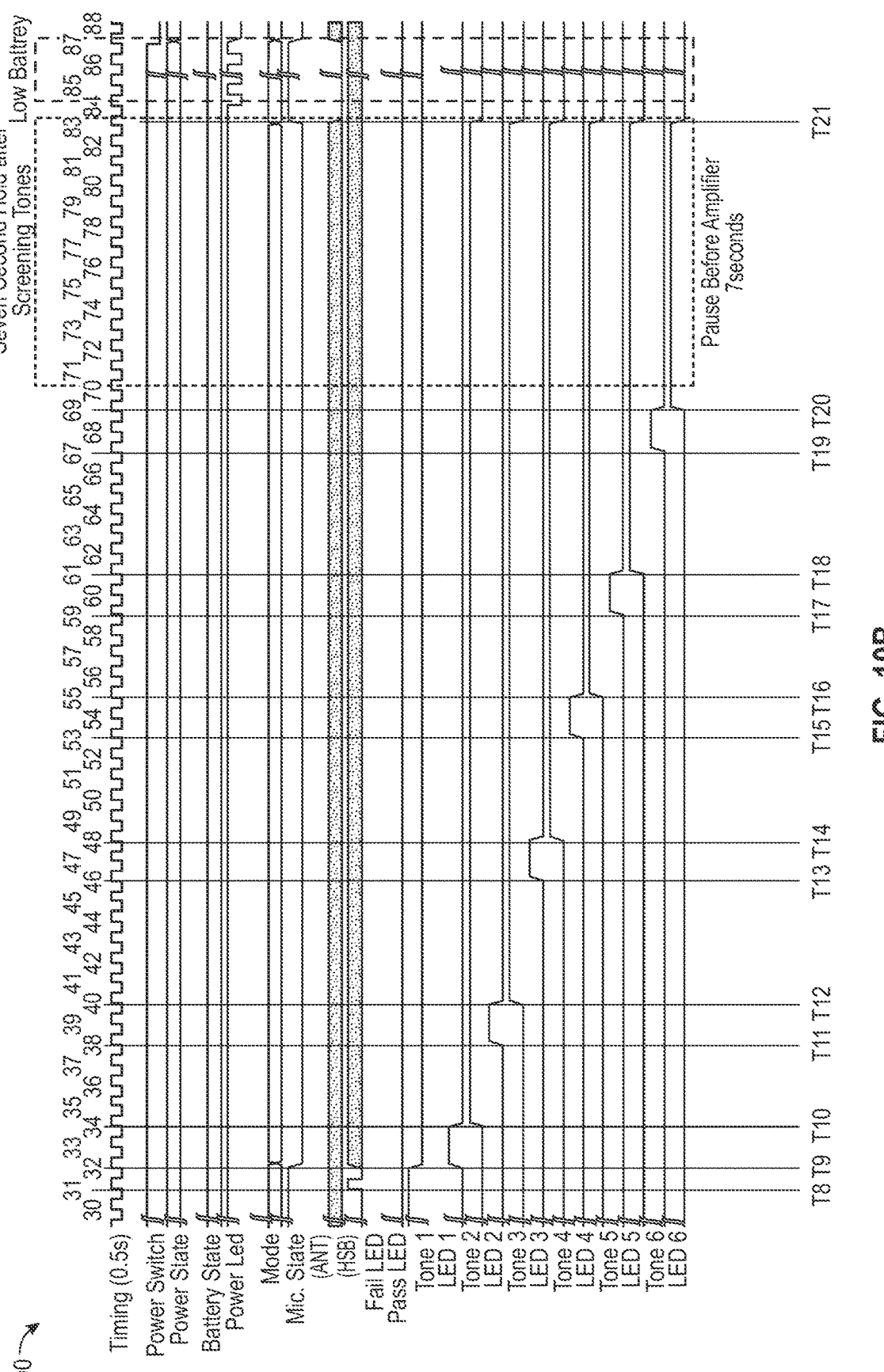

FIGS. 9A-E illustrate a portable hearing screening and amplification device 1' according to one particular embodiment of the disclosed concept. The portable hearing screening and amplification device 1' includes housing 6', a screening test front cover 6A', a jack 4 for the headset 2, power switch 16 and a volume adjuster 20'. The portable hearing screening and amplification device 1' also includes a user interface 17, which is covered by the screening test front cover 6A' during non-use of the device 1' or the amplification mode. The user interface 17 includes an ambient noise test (ANT) button 12A, hearing screening button 12B, ANT status indicators 13 and hearing screening test indicators 14, which are discussed further in detail below. FIG. 9A is a front view of the portable hearing screening and amplification device 1'. FIG. 9A is a front view of the portable hearing screening and amplification device 1' with the screening test front cover open 6A', depicting the user interface 17. FIG. 9C is a side view of the portable hearing screening and amplification device 1'. FIG. 9D is another side view of the portable hearing screening and amplification device 1'. FIG. 9E is a perspective view of the portable hearing screening and amplification device 1' with the open screening test front cover 6A'. The power switch 16 may include or be adjacent to a power indicator (not shown) structured to be lit upon turning on of the portable hearing screening and amplification device 1'. The power indicator may be an LED, which remains lit steadily upon turning on the portable hearing screening and amplification device 1'. If the battery 26 is low, the power indicator is structured to flash to alert the user to replace the battery 26. In some examples, the portable hearing screening and amplification device 1' may also include a clip (not shown) for the user to easily fasten the portable hearing screening and amplification device 1' on his or her belt, clothing, etc. for use during the amplification mode.

For operation, a screener (e.g., without limitation, a clinician, an examiner) turns on the portable hearing screening and amplification device 1' by actuating the power switch 16' (e.g., without limitation, sliding the power switch 16'). Upon turning on of the portable hearing screening and amplification device 1', the portable hearing screening and amplification device 1' is set automatically in the amplification mode. The screener may then open the screening test front cover 6A' and actuate ANT button 12A to commence the ambient noise test. Upon passing of the ANT test, the user (the individual who is being screened for hearing status) may undergo the hearing screening based on the actuation of the hearing screening button 12B. During the hearing screening, a number of screening tones (e.g., without limitation, three tones for each ear) are tested. Upon completion of the hearing screening, the portable hearing screening and amplification device 1' switches automatically from the hearing screening mode to the amplification mode based on a timing algorithm. For example, after a preset period (e.g., without limitation, seven seconds) upon the completion of the hearing screening, the portable hearing screening and amplification device 1' reverts back to the amplification mode. This sequence of the hearing screening as well as the switching of modes are discussed further in detail with respect to the timing diagrams as shown in FIGS. 10A-B.

The portable hearing screening and amplification device 1' is similar to the portable hearing screening and amplification device 1 of FIGS. 1-4, except that the portable hearing screening and amplification device 1' (i) includes a single microcontroller (not shown) for the operation of the portable hearing screening and amplification device 1' in tandem with the headset 2; (ii) includes a digital microphone with the built-in functions (e.g., without limitation, detecting and amplifying background noises, computing the background noise levels); (iii) does not include a look-up table 620; (iv) does not include a display power switch 8; and (v) has a more user-friendly design (e.g., without limitation, a smaller user interface 17, a smaller and easy to grab housing 6'). For brevity, the overlapping description of similar features are omitted and the differences are described further in detail below.

Figure 11:
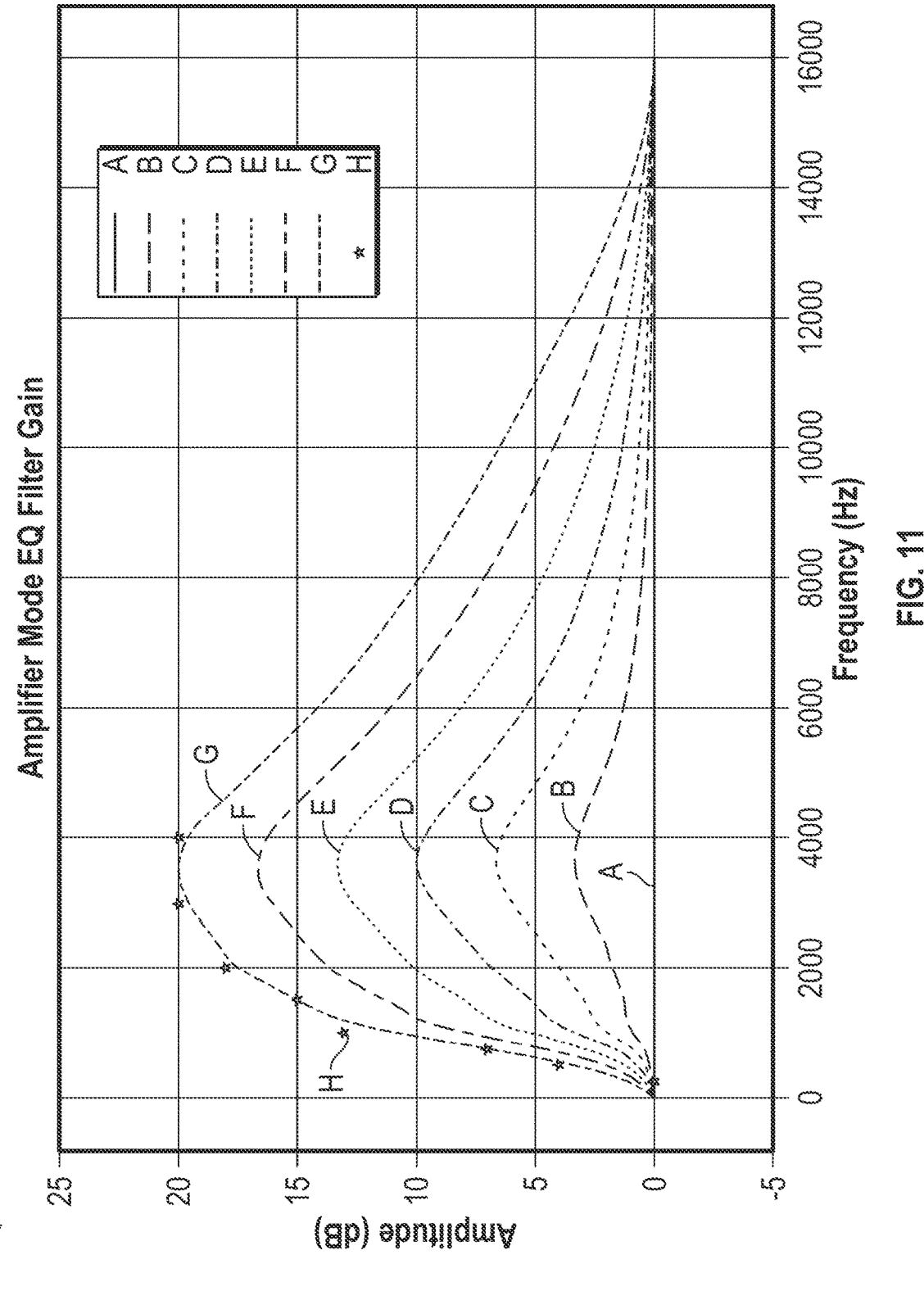
FIG. 11 illustrates amplification mode filter gains according to one particular, non-limiting exemplary embodiment of the disclosed concept.

The single microcontroller performs the functionalities of both the main controller 30 and subcontroller 32 shown in FIG. 4, thereby increasing efficiency and reducing costs. The digital microphone has built-in functions (e.g., without limitation, detecting background noises, computing the background noise levels, and detecting sound for amplification) and is programmable, allowing the portable hearing screening and amplification device 1' to have programable equalization. As such, frequency and volume adjuster-based gain settings may be applied. The amplifier mode equalization filter gain is illustrated in FIG. 11. Further, a look-up table 620 is not needed since a sound pressure level (SPL) calibration may be used without using the look-up table 620. That is, the controller is calibrated to a white noise (uniform power across all audible frequencies) source with a known volume. During the ambient noise test, any sound picked up by the microphone above an ambient noise test threshold triggers a failed ANT. The ambient noise test threshold may be root means square dB SPL (A weighted) for specific noises and represent minimal masking level, i.e., the level at which 35 dB high level could no longer be heard. For example, 49 dB sound pressure level (SPL) may trigger "No Go", measured at a distance of, e.g., without limitation, 1.22 meters (48 inches) from a speaker.

The portable hearing screening and amplification device 1' does not include a display power switch 8 shown in FIG. 1 since the status indicators (e.g., the ANT indicators 13 and hearing screening test indicators 14) are activated automatically upon actuation of the ambient noise test button 12A and the hearing screening button 12B, respectively. When the screening location (e.g., without limitation, a screening room, a clinic) fails the ANT, the ANT fail indicator (e.g., without limitation, a red LED) is lit and the user may actuate the ANT button 12A again. When the ANT is passed, the ANT pass indicator (e.g., without limitation, a white LED) is lit and the user may actuate the hearing screening button 12B within a predefined period (e.g., without limitation, 5 minutes). When the hearing screening button 12B is actuated, the screening tones (e.g., without limitation, three tones at 1000 Hz, 2000 Hz, or 4000 Hz) are tested sequentially and corresponding hearing screening test indicators 14 are lit sequentially and automatically (as illustrated in FIGS. 9B and 10B). The hearing screening indicators 14 include six LEDs (three LEDs for the three screening tones for left ear and three LEDs for the three screening tones for the right ear). When the portable hearing screening and amplification device 1' reverts back to the amplification mode, these indicators 13,14 are no longer lit. In some examples, the portable hearing screening and amplification device 1' may include a plug (e.g., without limitation 3.5 mm phone plug) and enter a low power state when the headset 2 is not coupled to the portable hearing screening and amplification device 1'. The screening test front cover 6A' may also include instruction label, which provides instruction on how to use the portable hearing screening and amplification device 1'.

By simplifying the user interface, utilizing timing algorithm, e.g., without limitation, automating switching of the modes, and removing unnecessary hardware and firmware components (e.g., display power switch 8, look-up table 620), the portable hearing screening and amplification device 1' in accordance with the present disclosure further improves efficiency and convenience as well as reducing the manufacturing cost as compared to the portable hearing screening and amplification device 1.

FIGS. 10A-B illustrate a timing diagram 1000 according to one particular embodiment of the disclosed concept. In FIG. 10, time interval is 0.5 second. However, this is for illustrative purposes only and any other time interval may be used depending on the circumstances and needs. At time T1, a screener (e.g., without limitation, a clinician, an examiner) actuates the power switch 16 and turns on the portable hearing screening and amplification device 1'. At time T2, the screener actuates the ANT button 12A and the ANT commences at time T3. At time T4 (approximately 3 seconds passed from T3), it is determined that the screening location has failed the ANT test and the ANT fail indicator is lit for approximately three seconds. At time T5, the screener actuates the ANT button 12A again to repeat the ANT and at time T6 the ANT commences again. At time T7, it is determined that the screening location has passed the ANT, the ANT pass indicator is lit and a predefined wait period (e.g., without limitation, 5 minutes) commences. The portable hearing screening and amplification device 1' is configured to wait and/or detect actuation of the hearing screening button 12B, if any, during the predefined wait period. If the screener actuates the hearing screener button 12B, e.g., at time T8, the hearing screening is commenced at time T9. At the same time, the ANT pass indicator is turned off. While FIG. 10A shows the timing diagram including ANT passing 1020 and hearing screening actuation followed by an ANT failure 1010, it is for illustrative purposes only. As such, the screening location may pass the ANT at the first attempt or there may be more than one ANT failures and repeats depending on the circumstances and the locations.

The timing diagram 1000 continues in FIG. 10B, showing the hearing screening timing of a plurality of hearing screening tones and switching of the portable hearing screening and amplification device 1' back to the default amplification mode. Before the hearing screening has started, a user (the individual being screened for hearing status) is provided with instructions, e.g., without limitation, to count a number of hearing screening tones the user hears or recognizes before the screening starts. Once the hearing screening tone sequence starts, the sequence continues automatically through all of the hearing screening tones (e.g., without limitation, six hearing screening tones (three hearing screening tones for each ear)).

At time T9, testing of hearing screening tone L1 (e.g., without limitation, at 1000 Hz) for left ear is commenced. The user is presented with the hearing screening tone L1 for a predefined listening period (e.g., without limitation, one second) beginning at time T9 and terminating at time T10. At time T10, the hearing screening test indicator for L1 is lit, indicating that the user has just been presented with the hearing screening tone L1 for the predefined listening period. There is a first pause period for, e.g., without limitation, two seconds after time T10 and upon the lapse of the pause at time T11, testing of screening tone L2 (e.g., without limitation, at 2000 Hz) for left ear is commenced. The user is presented with the hearing screening tone L2 for the predefined listening period beginning at time T11 and terminating at time T12. At time T12, the hearing screening test indicator for L2 is lit, indicating that the user has just been presented with the hearing screening tone L2 for the predefined listening period. There is a second pause period for, e.g., without limitation, three seconds after time T12 and upon the lapse of the second pause at time T13, testing of screening tone L3 (e.g., without limitation, at 4000 Hz) for left ear is commenced. The user is presented with the hearing screening tone L3 for the predefined listening period beginning at time T13 and terminating at time T14. At time T14, the hearing screening test indicator for L3 is lit, indicating that the user has just been presented with the hearing screening tone L3 for the predefined listening period. There is a third pause period for, e.g., without limitation, 2.5 seconds after time T14 and upon the lapse of the pause at time T15, testing of screening tone R1 (e.g., without limitation, at 1000 Hz) for right ear is commenced.

The user is presented with the hearing screening tone R1 for the predefined listening period beginning at time T15 and terminating at time T16. At time T16, the hearing screening test indicator for R1 is lit, indicating that the user has just been presented with the hearing screening tone R1 for the predefined listening period. There is a fourth pause period for, e.g., without limitation, two seconds after time T16 and upon the lapse of the pause at time T17, testing of screening tone R2 (e.g., without limitation, at 2000 Hz) for right ear is commenced. The user is presented with the hearing screening tone R2 for the predefined listening period beginning at time T17 and terminating at time T18. At time T18, the hearing screening test indicator for R2 is lit, indicating that the user has just been presented with the hearing screening tone R2 for the predefined hearing period. There is a fifth pause period for, e.g., without limitation, three seconds after time T18 and upon the lapse of the pause at time T19, testing of screening tone R3 (e.g., without limitation, at 4000 Hz) for right ear is commenced. The user is presented with the hearing screening tone R3 for the predefined listening period beginning at time T19 and terminating at time T20. At time T20, the hearing screening test indicator for R3 is lit, indicating that the user has just been presented with the hearing screening tone R3 for the predefined listening period. There is a sixth pause period for, e.g., without limitation, seven seconds after time T20, and upon lapse of the sixth pause period at time T21, the portable hearing screening and amplification device 1' reverts back to the amplification mode. At this time the screener may ask the user how many tones the user has heard and determines whether the user has passed or failed the hearing screening. The user may use the portable hearing screening and amplification device 1' as an amplification device as needed to improve communication during, e.g., without limitation, a health care visit. If the hearing screening has been failed, the screener may refer the user for more in-depth hearing assessment. It is noted that the timing including the duration of pauses and the predefined listening periods is for illustrative purposes only and may vary depending on the circumstances and needs. For example, the length of the pauses between tones may be randomized to vary between 0.5 and 2.5 sec each time the hearing screening is performed. FIG. 10B shows flashing of one or more of the power status indicator and the indicators 13,14 for, e.g., every 0.5 second in order to alert the screener or the user to replace the battery 26.

As illustrated in these timing diagrams, the ambient noise test and the hearing screening are performed accurately and effectively in short times (i.e., three seconds for ANT, one second for each tone testing and only up to three seconds pause in between the hearing screening tone testing) in any screening location convenient for the patient as compared to the traditional hearing screening that requires a special screening room equipped with expensive equipment and a long hearing screening time by a clinician with special training.

FIG. 11 illustrates amplification mode equalization filter gain according to one particular embodiment of the disclosed concept. The volume adjuster 20' may have a number of volume control levels (e.g., without limitation, six as shown in FIG. 11), however, this is for illustrative purposes only and there may be more or less volume control levels depending on the circumstances and needs. As shown in FIG. 11, as the volume increases, the gain increases. Graph A shows zero gain when there is zero volume control. Graph B shows respective gain of volume control level 1 (lowest volume increase). Graph C shows respective gain of volume control level 2. Graph D shows respective gain of volume control level 3. Graph E shows respective gain of volume control level 4. Graph F shows respective gain of volume control level 5. Graph G shows respective gain of volume control level 6 (highest volume increase), showing gain of 20 at a specific frequency (at approximately 3500 Hz). Graph H shows example maximum gain levels, obtained from simulation.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A portable hearing screening and amplification device structured to be coupled to a headset, comprising:

a housing, a plurality of buttons, a plurality of indicators, a display circuit, a microphone circuit, an output circuit, a power source, and a controller, wherein the plurality of buttons comprises a background noise test switch structured to activate a background noise test, a hearing screening switch structured to commence hearing screening based at least in part on passing of the background noise test, a volume adjuster structured to enable amplification based on volume control levels and adjust a volume of a speaker of the headset, and a power button structured to turn on and off the portable hearing screening and amplification device;

wherein the controller is coupled to the display circuit, the output circuit coupled to the speaker, the plurality of hearing screening indicators, the microphone circuit, and the plurality of indicators, the controller structured to control signal processing related to the microphone circuit, the output circuit, the hearing screening, and the amplification;

wherein based at least in part on a successful completion of a background noise test, the portable hearing screening and amplification device is structured to transmit a plurality of hearing screening tones to the headset for a user for testing of the plurality of hearing screening tones, and complete the hearing screening based on responses of the user related to the plurality of hearing screening tones, the responses including a number of hearing screening tones that the user has perceived during the hearing screening; and wherein based on a determination that the number of hearing screening tones perceived by the user is less than a prerequisite number, the portable hearing screening and amplification device is further structured to switch to amplification mode and perform the amplification based on a volume control level of the volume adjuster.

2. The portable hearing screening and amplification device according to claim 1, wherein portable hearing screening and amplification device is further structured to be used during a healthcare visit comprising inpatient stay, senior living intake assessment, emergency room visit, home health visit, or a routine check-up.

3. The portable hearing screening and amplification device according to claim 1, wherein the portable hearing screening and amplification device comprises a size less than or equal to a size of a hand-held device.

4. The portable hearing screening and amplification device according to claim 1, wherein the amplification mode is the default mode and the portable hearing screening and amplification device is further structured to be set automatically in the amplification mode upon turning on of the portable hearing screening and amplification device and revert automatically to the amplification mode upon completion of the hearing screening based on a preset timing sequence.

5. The portable hearing screening and amplification device according to claim 4, wherein the hearing screening including the testing of the plurality of screening tones is performed based on the preset timing sequence.

6. The portable hearing screening and amplification device according to claim 1, wherein the plurality of indicators comprises a status indicator structured to indicate status of the portable hearing screening and amplification device including a pass or fail of the background noise test, a plurality of hearing screening indicators structured to indicate respective status of the plurality of hearing screening tones, and a power indicator structured to indicate power status of the portable hearing screening and amplification device.

7. The portable hearing screening and amplification device according to claim 1, wherein the plurality of hearing screening tones comprises frequencies within a primary hearing range including 1 kHz, 2 kHz, and 4 kHz that are prone to hearing loss.

8. The portable hearing screening and amplification device according to claim 1, wherein a period of the testing of each hearing screening tone is less than or equal to 90 seconds.

9. The portable hearing screening and amplification device according to claim 1, wherein the controller comprises a calibrated sound pressure level threshold derived from background noise sound data collected from a plurality of environments and predetermined voltage levels associated with background noise thresholds and the plurality of environments.

10. The portable hearing screening and amplification device according to claim 1, wherein a background noise having a sound pressure level above the calibrated sound pressure level threshold fails the background noise test and a background noise having the sound pressure level less than or equal to the calibrated sound pressure level threshold passes the background noise test.

11. The portable hearing screening and amplification device according to claim 1, wherein at least one of the microphone circuit, the output circuit, or the headset is calibrated, the microphone circuit calibrated to collect an output voltage of the microphone circuit for background noise test thresholds, the output circuit calibrated to control output signal delivered to the headset, and the headset calibrated to transmit at least the plurality of hearing screening tones.

12. The method of claim 11, wherein the portable hearing screening and amplification device is further structured to be used during a healthcare visit comprising inpatient stay, senior living intake assessment, emergency room visit, home health visit, or a routine check-up.

13. The method of claim 11, wherein the portable hearing screening and amplification device comprises a size less than or equal to a size of a hand-held device.

14. The method of claim 11, wherein the amplification mode is the default mode and the portable amplification and hearing screening is further structured to be set automatically in the amplification mode upon turning on of the portable hearing screening and amplification device and revert automatically to the amplification mode upon completion of the hearing screening based on a preset timing sequence.

15. The method of claim 11, wherein the controller comprises a calibrated sound pressure level threshold derived from background noise sound data collected from a plurality of environments and predetermined voltage levels associated with background noise thresholds and the plurality of environments and wherein a background noise having a sound pressure level above the calibrated sound pressure level threshold fails the background noise test and a background noise having the sound pressure level less than or equal to the calibrated sound pressure level threshold passes the background noise test.

16. The method of claim 15, further comprising:
checking for a source of background noise detected upon failing the background noise test;
determining that the background noise detected is capable of being isolated; and
reactivating the background noise test switch upon isolating the detected background noise.

17. The method of claim 15, further comprising:
checking for a source of background noise detected upon failing the background noise test;
determining that the background noise detected is not capable of being isolated; and
finding a different screening location based on a determination that the background noise detected is not capable of being isolated.

18. The method of claim 11, further comprising:
indicating at least one of status of the portable hearing screening and amplification device including pass or fail state of the background noise test, status of the plurality of hearing screening tones or a power status of the portable hearing screening and amplification device.

19. A method for providing amplification and hearing screening using a portable hearing screening and amplification device coupled to a headset, comprising:
turning on the portable hearing screening and amplification device comprising a housing, a plurality of buttons, a plurality of indicators, a display circuit, a microphone circuit, an output circuit, a power source, and a controller, wherein:
the plurality of buttons comprises a background noise test switch structured to activate a background noise test, a hearing screening switch structured to commence hearing screening based at least in part on passing of the background noise test, a volume adjuster for enabling amplification and adjusting a volume of a speaker of the headset, and a power button for turning on and off the portable hearing screening and amplification device; and
the controller is coupled to the display circuit, the output circuit, the plurality of hearing screening indicators, the microphone circuit, the plurality of indicators and the speaker, and is structured to control signal processing related to the microphone circuit, the hearing screening, and the amplification;
activating a background noise test switch based on a user input to determine that a screening location passes or fails a background noise test;
transmitting, upon passing the background noise test, a plurality of hearing screening tones to a user via the headset for testing of each hearing screening tone;
completing the hearing screening based on responses of the user related to the plurality of hearing screening tones, the responses including a number of hearing screening tones that the user has perceived during the hearing screening;
determining whether the user has perceived a requisite number of hearing screening tones; and
based on a determination that the number of hearing screening tones perceived by the user is less than a prerequisite number, switching to amplification mode from hearing screening mode and performing the amplification based on a volume control level of the volume adjuster.

20. A method for providing amplification and hearing screening using a portable hearing screening and amplification device coupled to a headset, comprising:
turning on the portable hearing screening and amplification device;
activating a background noise test switch based on a user input to determine that a testing area passes or fails a background noise test;
transmitting, upon passing the background noise test, a plurality of hearing screening tones to a user via the headset;
determining whether the user has perceived a requisite number of hearing screening tones; and
switching to an amplification mode based on the determination that the user has perceived less than the requisite number of hearing screening tones;
adjusting a volume of the headset in accordance with hearing capacity of the user; and recommending to the user a comprehensive hearing test based on the hearing screening.

* * * * *